United States Patent
Hirosawa

[11] Patent Number: 6,151,116
[45] Date of Patent: Nov. 21, 2000

[54] EVALUATION METHOD FOR THIN FILM MOLECULAR ORIENTATION, EVALUATION APPARATUS FOR THE ORIENTATION AND RECORDING MEDIUM

[75] Inventor: Ichiro Hirosawa, Tokyo, Japan

[73] Assignee: NEC Corporation, Tokyo, Japan

[21] Appl. No.: 09/391,049

[22] Filed: Sep. 7, 1999

[30] Foreign Application Priority Data

Sep. 7, 1998 [JP] Japan .................... 10-252662

[51] Int. Cl.[7] .......................... G01N 21/00; G01N 21/55; G01J 4/00
[52] U.S. Cl. ..................... 356/369; 356/445; 356/237
[58] Field of Search ................... 356/369, 445, 356/237

[56] References Cited

U.S. PATENT DOCUMENTS

| | | | |
|---|---|---|---|
| 4,585,348 | 4/1986 | Chastang et al. | 356/369 |
| 5,402,237 | 3/1995 | Rhiger et al. | 356/369 |
| 5,408,322 | 4/1995 | Hsu et al. | 356/369 |
| 5,689,332 | 11/1997 | Ellingson et al. | 356/237 |
| 5,838,453 | 11/1998 | Ohsaki et al. | 356/445 |
| 5,984,185 | 11/1999 | Dickson et al. | 235/457 |

FOREIGN PATENT DOCUMENTS

| | | |
|---|---|---|
| 3-65637 | 3/1991 | Japan . |
| 4-32933 | 11/1992 | Japan . |
| 5-5699 | 1/1993 | Japan . |
| 8-152307 | 6/1996 | Japan . |
| 09218133 | 8/1997 | Japan . |
| 9-218133 | 8/1997 | Japan . |

OTHER PUBLICATIONS

Canillas et al, Phase–Modulated ellipsometer using a Fourier transform infrared spectrometer for real time applications, Aug. 1993, Review of Scientific Instruments, pp. 2153 and 2155.

"Correlation between the pretilt angle of liquid crystal and the inclination angle of the polyimide backbone structure", by R. Arafune, et al., Appl. Phys. Lett. 71 (19), Nov. 10, 1997, pp. 2755–2757.

"In situ infrared ellipsometry study of hydrogenated amorphous carbon/Si interface formation", by T. Heitz, et al., Applied Physics Letters, No. 72, No. 7, Feb. 16, 1998, pp. 780–782.

"Determination of the composition and thickness of borophosphosilicate glass films by infrared ellipsometry", by R. Ossikovski, et al., Appl. Phys. Lett. 65 (10), Sep. 5, 1994, pp. 1236–1239.

"Bragg Reflection of Light from Single–Domain Cholesteric Liquid–Crystal Films", by D. W. Berreman, et al., Physical Review Letters, vol. 25, No. 9, Aug. 31, 1970, pp. 576–581.

*Primary Examiner*—Frank G. Font
*Assistant Examiner*—Armando Rodriguez
*Attorney, Agent, or Firm*—Scully, Scott, Murphy & Presser

[57] ABSTRACT

Dependency of the polarization state of a reflected infrared ray generated when an infrared ray in a fixed polarization state is incident on a sample thin film on incidence orientation is measured while rotating the sample thin film in a plane parallel to a surface thereof. Next, an optical anisotropy of the sample thin film is determined based on the dependency of the polarization state on the incidence orientation. Then, the state of molecular orientation in the sample thin film is determined based on the optical anisotropy.

26 Claims, 14 Drawing Sheets

EVALUATION METHOD FOR THIN FILM MOLECULAR ORIENTATION, EVALUATION APPARATUS FOR THE ORIENTATION AND RECORDING MEDIUM

BACKGROUND OF THE INVENTION

1. Field of the Invention

The present invention relates to a method and an apparatus of evaluating the state of molecular orientation of a thin film having anisotropic molecular orientation such as a liquid crystal alignment film in which initial orientation is applied to liquid molecules, and for recording medium for such a method and an apparatus.

2. Description of the Related Art

To evaluate a thin film having anisotropic molecular orientation (anisotropic thin film), various types of methods have been proposed thus far. As for the method using visible light, there is proposed, for example, a method of measuring the incidence angle dependency of the intensity of reflection light generated when a plurality of wavelengths are incident (Japanese Patent Application Laid-Open No. Hei 5-5699 and No. Hei 4-329333). There are also proposed a method of measuring the dependency of the intensity of reflection light on incidence angle and on incidence orientation (Japanese Patent Application Laid-Open No. Hei 3-65637) and a method of efficiently measuring the dependency of the intensity of reflection light generated from incidence light having only S polarization component and that having only P polarization component, on incidence angle and incidence orientation (Japanese Patent Application Laid-Open No. Hei 8-152307). Further, there is proposed a method of determining a dielectric constant, a film thickness and a direction of a principal dielectric constant coordinate of an oriented part, and a dielectric constant and a film thickness of a non-oriented part while rotating a sample in a plane, from the incidence orientation dependency of the polarization state of reflection light (Japanese Patent Application Laid-Open No. Hei 9-218133).

According to the methods using visible light rays, it is possible to quantitatively evaluate crystal orientation equivalent to molecular orientation for an inorganic thin film having high crystallinity since the correlation between the crystal structure and optical anisotropy for most of thin films has already been known. According to the method disclosed by Japanese Patent Application Laid-Open No. Hei 08-218133, in particular, not only optical anisotropy but also the thickness of a sample can be determined.

An organic thin film, by contrast, has normally very low crystallinity and, therefore, it is difficult to determine molecular orientation from the optical anisotropy of the film. In case of a polymer thin film typically represented by a liquid crystal alignment film, in particular, it is considered that molecular chains are mutually twisted. Due to this, the optical characteristics of a basic unit forming a polymer chain does not necessarily accurately reflect those of a polymer chain. That is, the molecular orientation of a thin film having low crystallinity, i.e., a polymer organic thin film such as a liquid crystal alignment film cannot be determined by measuring the optical anisotropy using a visible light ray.

To evaluate the state of molecular orientation of an organic thin film, an infrared absorption spectrometry using a linearly polarized infrared ray is widely carried out. This method is disclosed by, for example, R. Arafune et al.: "Appl. Phys. Lett., 71, 2755(1997)". This method is intended to measure the variation of the intensity of the infrared ray with respect to the relative angle between the polarization orientation of an infrared ray which has passed through a sample and sample orientation. That is to say, this method is intended to evaluate orientation by detecting dichroism that infrared absorption amount varies with molecular orientation. However, the application of this method is limited to a film formed on a substrate, such as a silicon substrate and a calcium fluoride (fluorite: $CaF_2$) substrate transmitting infrared rays. Since an infrared ray is not transmitted by a glass substrate, the molecular orientation state of a film, such as a liquid crystal alignment film, formed on a glass substrate cannot be measured by this method.

In recent years, infrared ellipsometry for evaluating wavelength dispersion of the polarization state of reflection light generated when an infrared ray is applied onto the surface of a thin film, has been developed. The evaluation of bonding state of a silicon substrate and a carbon film is disclosed (T. Heitz et al.,: "Appl. Phys. Lett., 72, 780 (1998)". In addition, a method of evaluating the film thickness and composition of a boronphosphosilicate glass (BPSG) on a silicon substrate is disclosed (R. Ossikovski et al.: "Appl. Phys. Lett., 65, 1236 (1994)). According to these methods, reflecting molecular orientation, a polarization state greatly changes at a specific infrared absorbing wavelength. Thus, information on chemical composition as in the same manner as infrared absorption spectrometry can be obtained. Besides, a sample on a glass substrate can be measured.

However, these methods are applicable only to an isotropic film.

As stated above, although the methods using visible light can be appropriately applied to an inorganic thin film having high crystallinity, they cannot be applied to the measurement of the molecular orientation state of an organic thin film. With the method using infrared absorption, the molecular orientation of a thin film formed on, for example, a glass substrate which does not transmit infrared cannot be measured. With the infrared spectroscopic ellipsometry, a sample on a glass substrate can be measured but a thin film having anisotropic molecular orientation cannot be evaluated.

Therefore, there exists no method of measuring the molecular orientation state of an organic thin film, such as a liquid crystal alignment film, having anisotropy and formed on a glass substrate under these circumstances.

SUMMARY OF THE INVENTION

It is an object of the present invention to provide an evaluation method and an evaluation apparatus for a thin film molecular orientation capable of obtaining the molecular orientation state of an organic thin film having anisotropy and formed on an arbitrary substrate and a recording medium for the evaluation.

According to one aspect of the present invention, a method of evaluating molecular orientation in a thin film may comprise the step of analyzing dependency of a polarization state of a reflected infrared ray which is generated when an infrared ray in a fixed polarization state is incident on a sample thin film on incidence orientation, while rotating the sample thin film in a plane parallel to a surface thereof. The method further comprises the steps of determining optical anisotropy of the sample thin film based on the dependency of the polarization state on incidence orientation, and determining a state of molecular orientation in the sample thin film based on the optical anisotropy.

According to another aspect of the present invention, an apparatus for evaluating molecular orientation in a thin film may comprise a light source which generates an infrared ray in a fixed polarization state and causes the infrared ray to be incident on a sample thin film; a rotary stage which rotates the sample thin film in a plane parallel to a surface thereof; and a detector which detects an infrared ray reflected from the sample thin film. The apparatus further comprises an analyzer which analyzes dependency of a polarization state of the reflected infrared ray detected by the detector on incidence orientation, while the rotary stage rotating the sample thin film in the plane parallel to the surface thereof, determines optical anisotropy of the sample thin film from the dependency of the polarization state on incidence orientation, and determines a state of molecular orientation in the sample thin film based on the optical anisotropy.

In the present invention, it is preferable to measure the incidence orientation dependency at a plurality of measurement points on the sample thin film and to obtain the in-plane distribution of the molecular orientation state of the sample thin film. The light source may include a Fourier transform infrared spectrometer and a polarizer. Further, since an infrared ray is used for the measurement, it is preferable that the sample thin film and optical paths of the incident infrared ray and the reflected infrared ray are arranged in a vacuum or an inert gas. An inert gas is at least one type of gas selected from, for example, a nitrogen gas and a rare gas.

According to the present invention, by analyzing the incidence orientation dependency of the polarization state of a reflection light generated when an infrared ray is incident on the sample surface, direct information on the molecular orientation of the thin film is obtained. When incidence orientation dependency at the same measurement point is measured, the rotary stage whose rotation axis passing the measurement point and perpendicular to the sample surface may hold the sample and the sample may be rotated using this stage. In addition, when measuring the in-plane distribution of molecular orientation, two stages parallel transiting in different orientations may be installed on the rotary stage, and the sample may be held on the stages. The measurement position on the sample surface is scanned by the parallel translation stages.

Also, by analyzing the measured incidence orientation dependency of the reflected infrared ray based on the matrix method using a matrix of four rows by four columns, it is possible to obtain direct information on the orientation state of a chemical region which may contribute to infrared absorption.

The polarization state of a reflection light can be calculated by the matrix of four rows by four columns. This calculation method is described in, for example, D. W. Berrman and T. J. Scheffer: "Phys. Rev. Lett., 25, 577(1970)".

According to this method, if light is incident on a sample at an incidence angle of $\beta$, the states of electromagnetic fields of incident light, reflection light and light transmitted through the substrate are represented by $\Phi_I$, $\Phi_r$ and $\Phi_t$, respectively, a matrix L of four rows by four columns and a film thickness d are used, then the following relationship is established in case of a film which has molecular orientation and uniaxial anisotropy:

$$\Phi_t = \exp(idL)(\Phi_I + \Phi_r).$$

Elements $\Delta_{14}$, $\Delta_{24}$, $\Delta_{31}$, $\Delta_{32}$, $\Delta_{33}$, $\Delta_{41}$, $\Delta_{42}$, $\Delta_{44}$ of the matrix L are zero. The remaining elements are as follows:

$\Delta_{11} = -(\epsilon_e - \epsilon_o) \sin \beta \sin \theta \cos \theta \sin \phi / (\epsilon_e \cos^2 \theta + \epsilon_o \sin^2 \theta)$,
$\Delta_{12} = 1 - \sin^2 \beta / (\epsilon_e \cos^2 \theta + \epsilon_o \sin^2 \theta)$,
$\Delta_{13} = (\epsilon_e - \epsilon_o) \sin \beta \sin \theta \cos \theta \cos \phi / (\epsilon_e \cos^2 \theta + \epsilon_o \sin^2 \theta)$,
$\Delta_{21} = \epsilon_o [\epsilon_e - (\epsilon_e - \epsilon_o) \sin^2 \theta \cos^2 \phi] / (\epsilon_e \cos^2 \theta + \epsilon_o \sin^2 \theta)$,
$\Delta_{22} = -\epsilon_o (\epsilon_e - \epsilon_o) \sin^2 \theta \cos^2 \phi / (\epsilon_e \cos^2 \theta + \epsilon_o \sin^2 \theta)$,
$\Delta_{23} = -\epsilon_o (\epsilon_e - \epsilon_o) \sin^2 \theta \cos \phi \sin \phi / (\epsilon_e \cos^2 \theta + \epsilon_o \sin^2 \theta)$,
$\Delta_{34} = 1$,
$\Delta_{43} = \epsilon_o [\epsilon_e - (\epsilon_e - \epsilon_o) \sin^2 \theta \sin^2 \phi] / (\epsilon_e \cos^2 \theta + \epsilon_o \sin^2 \theta) - \sin^2 \beta$, where $\epsilon_e$ and $\epsilon_o$ are dielectric constants represented by the principal dielectric constant coordinate system, $\theta$ is the gradient angle of the principal dielectric constant coordinate to the film surface, and $\phi$ is the in-plane orientation angle of the incident light.

In respect of calculation of the polarization state of the reflection light based on these formulas, if there is a difference between $\epsilon_e$ and $\epsilon_o$, it is indicated that anisotropy occurs to the polarization state of the reflection light. In addition, the difference in the angle of the principal dielectric constant coordinate to the film surface reflects the incidence orientation dependency. Therefore, the anisotropic dielectric constant and the gradient of the main axis can be determined from the measurement value of the incidence orientation dependency of the polarization state of the reflected infrared ray. Moreover, since absorption reflects the dielectric constant, the anisotropy of the direction of a structure unit contributing to infrared absorption can be determined.

The reason for using infrared radiation in the present invention is that, since an infrared ray correlates to molecular vibration, information on the direction (orientation state) of the molecular structure itself corresponding to molecular vibration can be obtained by using infrared radiation. That is, by using infrared radiation, a complex dielectric constant can be measured and, if the complex dielectric constant of the vibration of each molecule is already known, molecular orientation can be determined. If a polarization state is to be measured by using visible light or ultraviolet light, molecular orientation cannot be determined since the lights in such a wavelength range do not correlate to molecular vibration.

According to the present invention, by measuring the incidence orientation dependency of the polarization state of the reflected infrared ray, the molecular orientation state and thickness of an organic film such as a liquid crystal alignment film formed on a glass substrate can be determined. Also, by using a sample stage provided with parallel stages moving in different two directions on the rotary stage controlled by a computer, the in-plane distribution of the molecular orientation state can be automatically measured. Further, by using an elliptical aperture or a cylindrical mirror and thereby making the shape of the infrared ray applied onto the sample surface circular, the irregularities of measurement values resulting from the non-uniformity of the in-plane sample membrane can be reduced.

DESCRIPTION OF THE PREFERRED EMBODIMENTS

Figure 1:
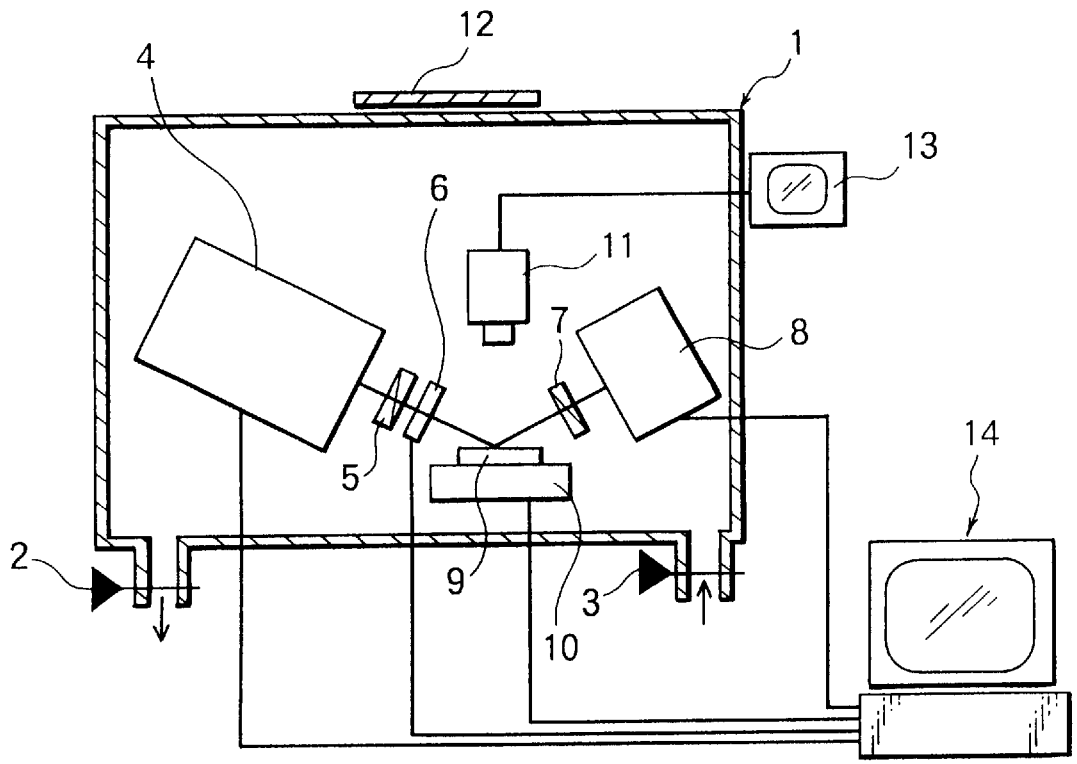
FIG. 1 is a typical view showing a structure of a molecular orientation evaluation apparatus in the first embodiment according to the present invention.

Now, an evaluation apparatus of evaluating molecular orientation in a thin film and an evaluation method using the evaluation apparatus in embodiments according to the present invention will be specifically described with reference to the accompanying drawings. FIG. 1 is a typical view showing a structure of a molecular orientation evaluation apparatus in the first embodiment according to the present invention.

In the first embodiment, important parts including optical devices such as a sample 9 and a detector 8 are contained in a container 1 so that an infrared optical path passes through an inert gas such as a rare gas or nitrogen gas or through a vacuum. A valve 2 provided at a gas inlet port, a valve 3 provided at a gas exhaust port and a door 12 for introducing the sample are provided at the container 1. An acrylic resin container or a stainless container with an inspection window having a thickness of 1 cm can be used as the container 1. In the container 1, an FT-IR (Fourier transform infrared) spectrometer 4 having an infrared source using a tungsten (W) filament and an interferometer included therein, is provided. For example, SPC-3200 of Bio-Rad Laboratories may be used as the FT-IR spectrometer 4. In this embodiment, a mirror is arranged at a sample part in the FT-IR spectrometer 4. This mirror allows an infrared ray to be introduced to the outside of the FT-IR spectrometer 4.

A stage 10, on which the sample 9 is mounted, is disposed in the container 1. A polarizer 5 and a photoelastic element 6 are arranged between the FT-IR spectrometer 4 and the stage 10 in this order. A detector 8 detecting an infrared ray reflected from the sample 9 is also arranged in the container 1. An analyzer 7 is arranged between the stage 10 and the detector 8. In the container, an infrared ray outputted from the FT-IR spectrometer 4 is incident on the sample 9 through the polarizer 5 and the photoelastic element 6. The infrared ray reflected by the sample 9 enters the detector 8 through the analyzer 7. The photoelastic element 6 modulates a polarization state at a modulation oscillation of, for example, 40 kHz. The detector 8 detects the intensity of an infrared ray.

Also, an autocollimator 11 detecting the gradient of the sample 9 with respect to the incident infrared ray is disposed in the container 1. To improve working efficiency for adjusting the gradient of the sample 9, a CCD camera is provided to monitor the position of a reflection light from the sample 9 and a display 13 for displaying a monitor image of the CCD camera is provided outside of the container 1.

The arrangement of the optical system is basically the same as that described in B. Drevillon et al., "Thin Solid Films", 236, 204 (1993) except for the provision of the container 1 and a structure of the stage 10.

Figure 2:
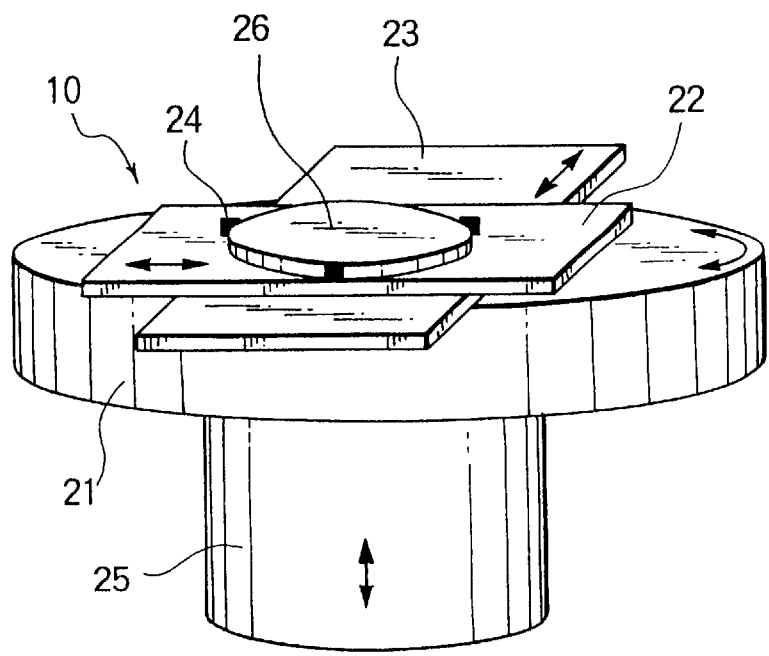
FIG. 2 is a typical view showing a structure of a stage 10.

Next, description will be given to the stage 10. FIG. 2 is a typical view showing a structure of the stage 2.

The stage 10 used in this embodiment is a combination of a rotary stage and two parallel translation stages for movement in rotation plane to adjust the orientation of the incidence of the infrared ray on the sample 9.

A rotary stage 21 for incident orientation adjustment is arranged such that the rotation axis thereof passes a position on a sample surface onto which the infrared ray is applied. Two parallel translation stages 22 and 23 are stacked on the rotary stage 21 so that their moving directions are orthogonal to the rotation axis and are orthogonal to each other. A mounting plate 26 for mounting a sample is provided on the upper parallel translation stage 22. A knob 24 for adjusting the optical tilt angle of the sample surface is provided at the mounting plate 26. If the knob 24 is adjusted, the gradient angle of the mounting plate 26 can be adjusted. Further, a parallel translation stag 25 moving in parallel to the rotation axis of the rotary stage 21 is provided below the rotary stage 21. Arrows in FIG. 2 indicate the moving directions of the rotary stage 21 and the parallel translation stage 22, 23 and 25, respectively.

The evaluation apparatus in this embodiment is also provided with a computer 14 for control, arranged outside of the container 1 to automatically measure the in-plane distribution of the anisotropy of a thin film formed on the surface of the sample 9. The computer 14 controls the operations of the FT-IR spectrometer 4, the photoelastic element 6, the detector 8 and the stage 10 as well as data input.

Apertures (not shown) for narrowing light beams are provided at the incidence side (FT-IR spectrometer 4 side) and the reflection side (detector 8 side) of the sample 9, respectively. Apertures may be, for example, circular apertures.

Next, the method of assembling the above-described evaluation apparatus will be described.

First, to determine the position of a measurement target sample, a mirror of 10 mm in diameter coated with, for example, gold (Au) is mounted on the surface at a sample position in a state in which the polarizer 5, the photoelastic element 6 and the analyzer 7 are not installed. Next, the height and position of the stage 10 are adjusted to maximize the intensity of the reflected infrared ray at the detector 8. Then, a plurality of pieces of polished optical glass each having a region coated with gold on the surface are prepared.

The optical glass pieces are mounted at the sample position so that the diameters of the gold-coated regions are gradually smaller, i.e., 5 mm, 3 mm and 1 mm. The above adjustments are repeated. While the intensity of the infrared ray reaches a maximum by adjustment using a mirror (an optical glass piece) having the gold-coated region of a diameter of 1 mm, the position of the autocollimator 11 is adjusted. Thereafter, the polarizer 5, the photoelastic element 6 and the analyzer 7 are mounted and adjustments are made again following the same procedures.

The above-stated steps are conducted in a state in which part of the sidewall of the container 1 maintaining an atmosphere is not provided. After the above-stated re-adjustments have been made, the sidewall is provided and the arranged position is checked.

Next, description will be given to the method of evaluating the anisotropy of the molecular orientation of a thin film for the sample, using the above-described evaluation apparatus, based on actually conducted measurements.

First, the method of preparing a sample will be described. Polyimide PI-C of Nissan Chemical Industries, Ltd. was spin-coated on a glass substrate (Corning Inc. 7059) and heated at 90° C. for 30 minutes and then at 250° C. for 60 minutes, thereby providing a sample C. Using an ellipsometer MARY-102 of Five Lab. Co., Ltd., the thickness of the polyimide film of the sample C was measured at an incidence angle of 70° and it measured 72 nm.

Thereafter, the sample C was subjected to rubbing processing twice at a penetration length of 0.05 mm, at a rotation speed of 800 rpm and at a substrate moving speed of 30 mm/s using a cloth roller of 50 mm in diameter. A sample which was not subjected to rubbing processing after baking was prepared as a reference sample, as well. Ten points on the surface of the sample which was not subjected to rubbing were measured with the ellipsometer with He-Ne laser as a light source. The film thickness measured 59±4 nm and a refractive index 1.62±0.1.

In this embodiment, while using an acrylic container 1, the two samples were measured. The shape of each aperture was circular. Measurement was conducted by introducing an argon (Ar) gas as an inert gas into the container 1. It took about 50 minutes for a peak resulting from moisture and remaining in the atmosphere to become less conspicuous. The height of the sample 9 was adjusted to maximize the intensity of the reflected infrared ray and the optical tilt angle was adjusted using the autocollimator 11.

Anisotropy was measured as follows. The incidence angle of the infrared ray with respect to the sample surface was set at, for example, 62° and the infrared ray which was linearly polarized by the polarizer 5 was applied onto the sample 9. With the analyzer 7 rotated, the infrared ray reflected from the sample 9 was detected by the detector 8 and the polarization state of the reflected infrared ray (the amplitude of an S component and that of a P component). As is well known, the S component is a polarization component parallel to the sample surface, whereas the P component is a polarization component orthogonal to the S component. The direction of the linear polarization by the polarizer 5 was set at a direction in which the amplitudes of the S and P components of the light incident on the sample 9 were equal to each other in a state in which the photoelastic element 6 did not modulate the polarization state. In this embodiment, the detector 8 detects an infrared ray synchronously with the operation of the FT-IR spectrometer 4, thereby making it possible to measure a polarization state for every wavelength.

In the evaluation of this measurement result, the reverse tangent $\psi$ $(=\tan^{-1}(A_P/A_S))$ of the amplitude ratio $(A_P/A_S)$ of the amplitude $A_S$ of the S component to the amplitude $A_P$ of the P component of the reflected infrared ray, and the phase difference $\Delta$ $(=\delta_P-\delta_S)$ between the phase $\delta_S$ of the S component and the phase $\delta_P$ of the P component were used as parameters indicating the polarization state of the light reflected by the sample.

The variation of the intensity of light detected by the detector 8 when the analyzer 7 was rotated, was measured. From the Fourier sum of the intensity of the light passing through the analyzer 7 at the analyzing angle, the reverse tangent $\psi$ of the amplitude ratio and the phase different $\Delta$ can be obtained. It is noted that since the phase difference $\Delta$ is a frequency function, two values are obtained as phase differences $\Delta$. Due to this, measurement was further continued by changing the polarization state using the photoelastic element 6. The value which had not changed even the polarization state was changed was adopted as a final value of the phase difference $\Delta$.

While changing the wave number (wavelength) of the infrared ray emitted from the FT-IR spectrometer 4, the reverse tangent $\psi$ and the phase difference $\Delta$ were measured. Then, the dependencies of the reverse tangent $\psi$ and the phase difference$\Delta$ on infrared wave number, i.e., wave number dispersions were obtained, respectively. At this moment, the sample 9 was rotated horizontally by the rotary stage 21 to thereby set the incident orientation at 0° or 60°, and wave number dispersions were obtained. It is noted that an incident orientation was expressed by a relative orientation to a reference orientation set at the rotary stage 21.

Figure 3:
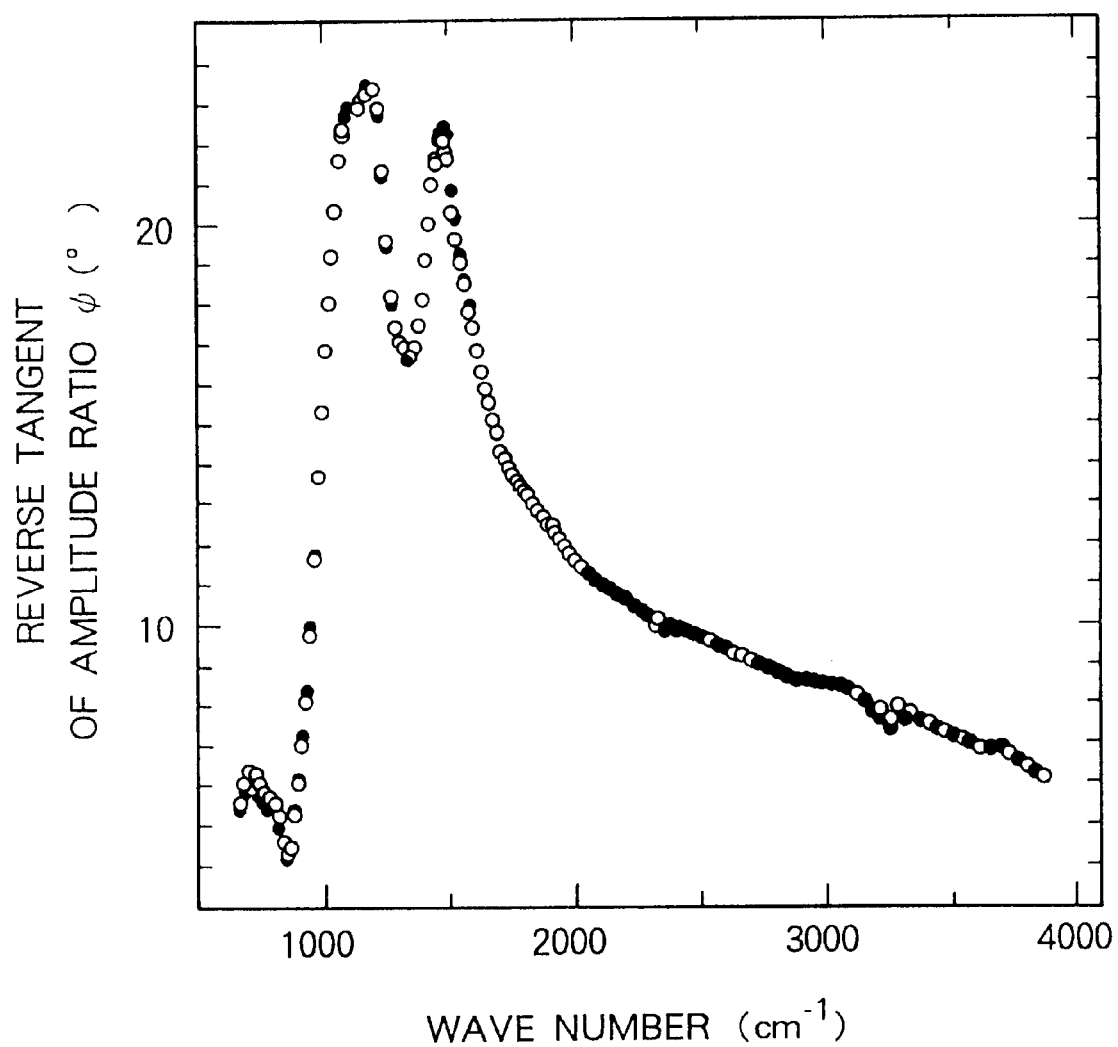
FIG. 3 is a graph showing a dependency of a reverse tangent $\psi$ of an amplitude ratio on infrared wave number for a sample which was not subjected to rubbing processing.
Figure 4:
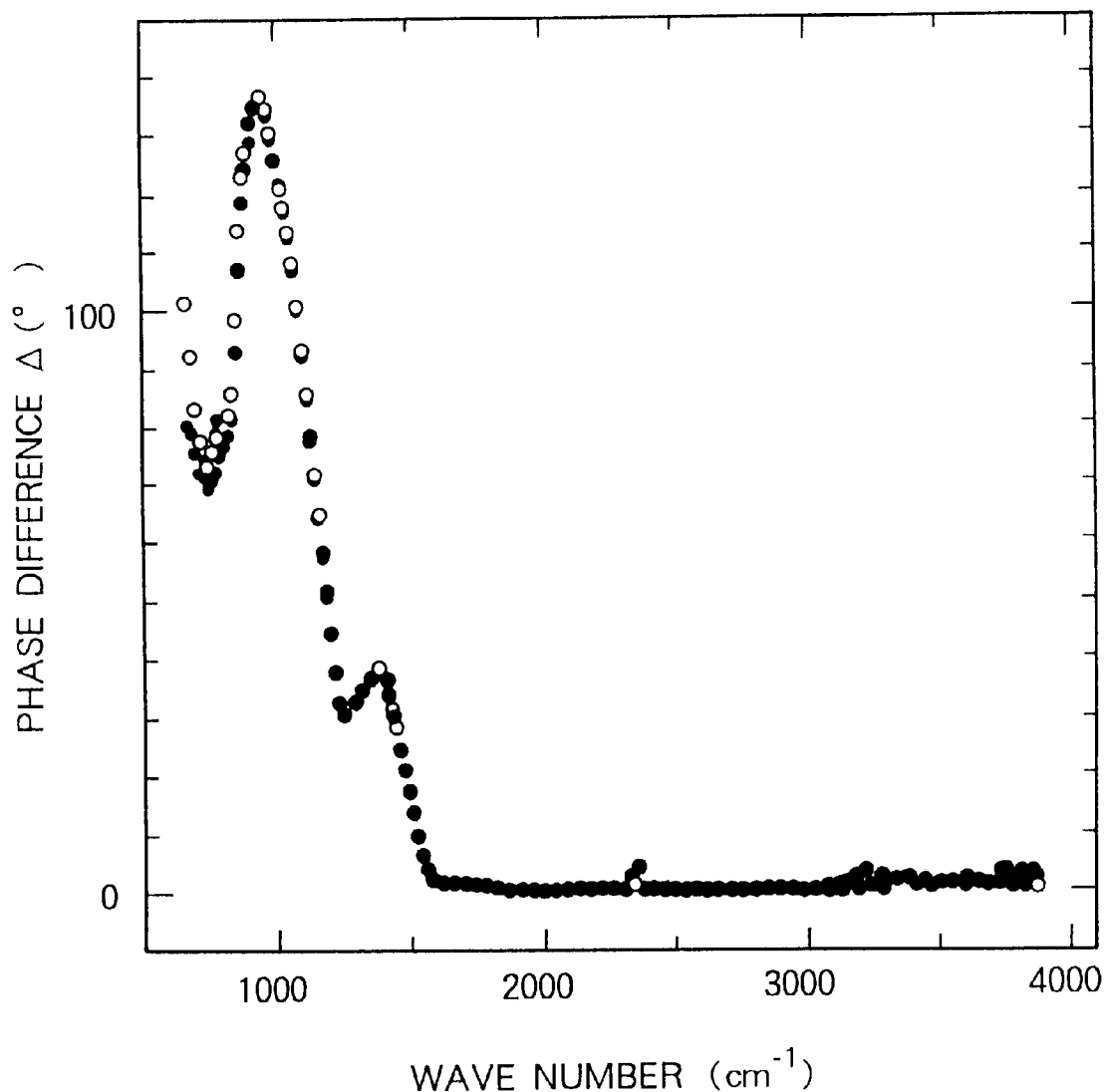
FIG. 4 is a graph showing a dependency of a phase difference $\Delta$ on infrared wave number for a sample which was not subjected to rubbing processing.
Figure 5:
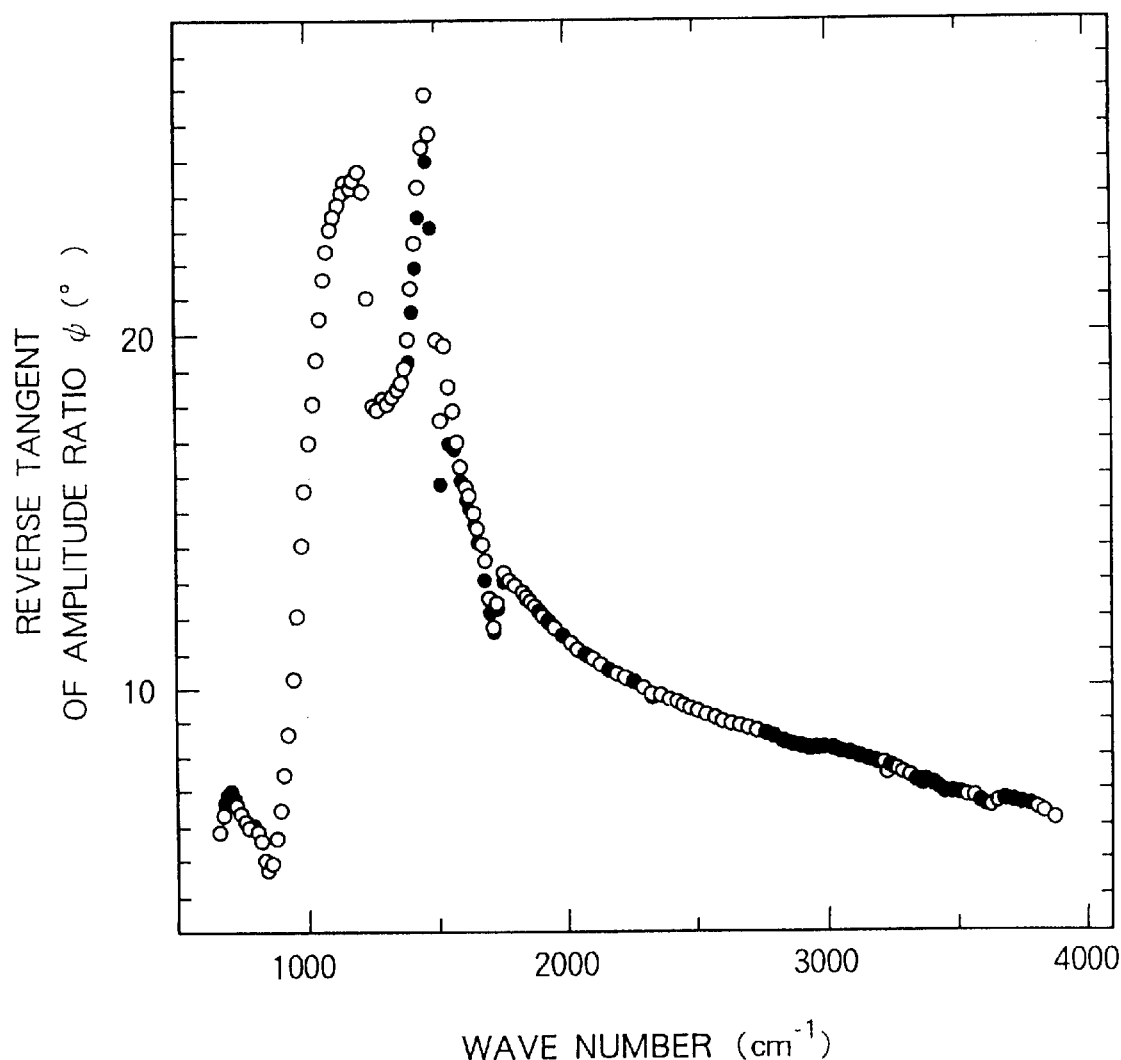
FIG. 5 is a graph showing a dependency of a reverse tangent $\psi$ of an amplitude ratio on infrared wave number for a sample which was subjected to rubbing processing.
Figure 6:
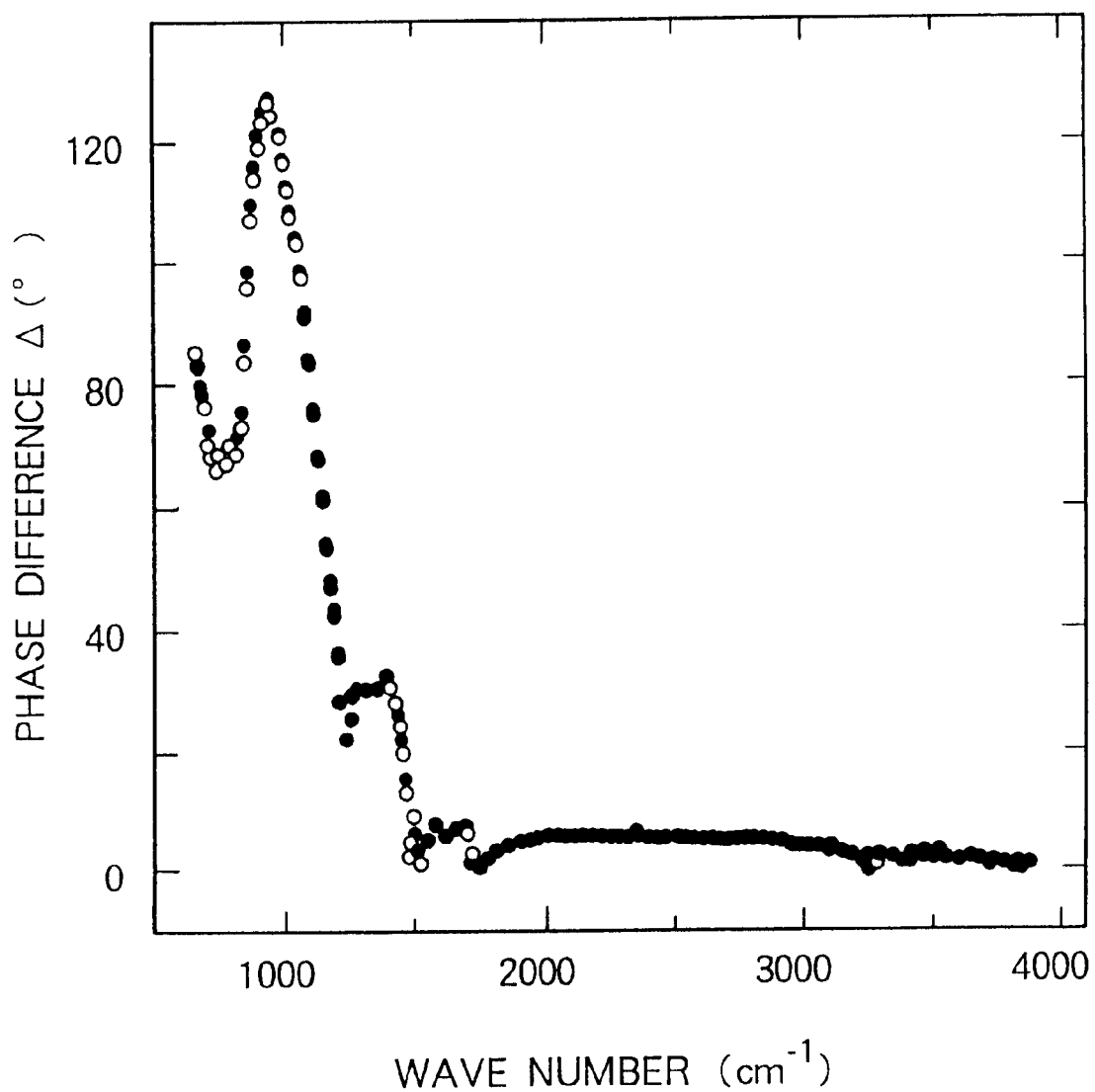
FIG. 6 is a graph showing a dependency of a phase difference Δ on infrared wave number for a sample which was subjected to rubbing processing.

FIG. 3 is a graph showing the dependency of the reverse tangent $\psi$ of an amplitude ratio on infrared wave number for the sample (reference sample) which was not subjected to rubbing processing. FIG. 4 is a graph showing the dependency of the phase difference $\Delta$ on infrared wave number for the sample (reference sample) which was not subjected to rubbing processing. On the other hand, FIG. 5 is a graph showing the dependency of the reverse tangent $\psi$ of an amplitude ratio on infrared wave number for the sample (sample C) which was subjected to rubbing processing. FIG. 6 is a graph showing the dependency of the phase difference $\Delta$ on infrared wave number for the sample (sample C) which was subjected to rubbing processing. In FIGS. 3 through 6, a symbol of white circle (○) indicates a result at an incident orientation of 0° and that of black circle (●) indicates the result at an incident orientation of 60°.

In FIGS. 3 and 4, which show the results of the reference sample with respect to an isotropic film, no significant difference was not seen between the incident orientation of 0° and that of 60°. In FIGS. 5 and 6, which show the results of the sample C with respect to an anisotropic film, a difference, though only a slight one, is seen between them if the fine structures in the neighborhood of the wave numbers 1500 cm$^{-1}$ and 1700 cm$^{-1}$ are noticed. Therefore, a fine structure, which was not observed on the sample which had not been subjected to rubbing, was observed on the sample for which anisotropy was considered to occur to molecular orientation due to rubbing. As can be understood from the above, according to the evaluation apparatus in this embodiment, it is possible to judge the presence/absence of the anisotropy of a film without measuring incident orientation dependency.

Next, incident orientation dependency was measured at the intervals of 60° for the sample (reference sample) which had not been subjected to rubbing and the sample (sample C) subjected to rubbing processing by operating the rotary stage 21.

Figure 7:
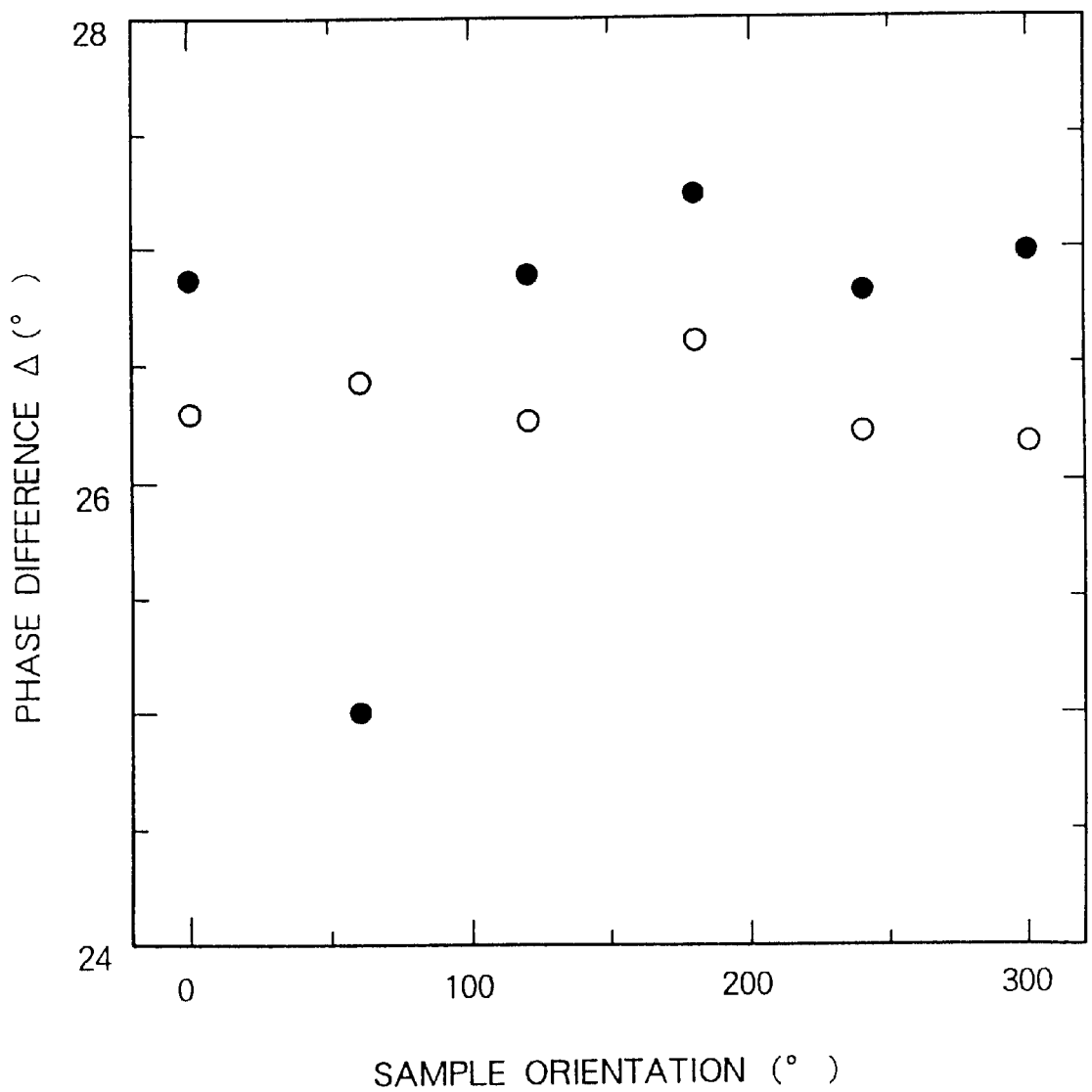
FIG. 7 is a graph showing an incidence orientation dependency of a phase difference Δ for a peak at a wave number of 1500 cm$^{-1}$.
Figure 8:
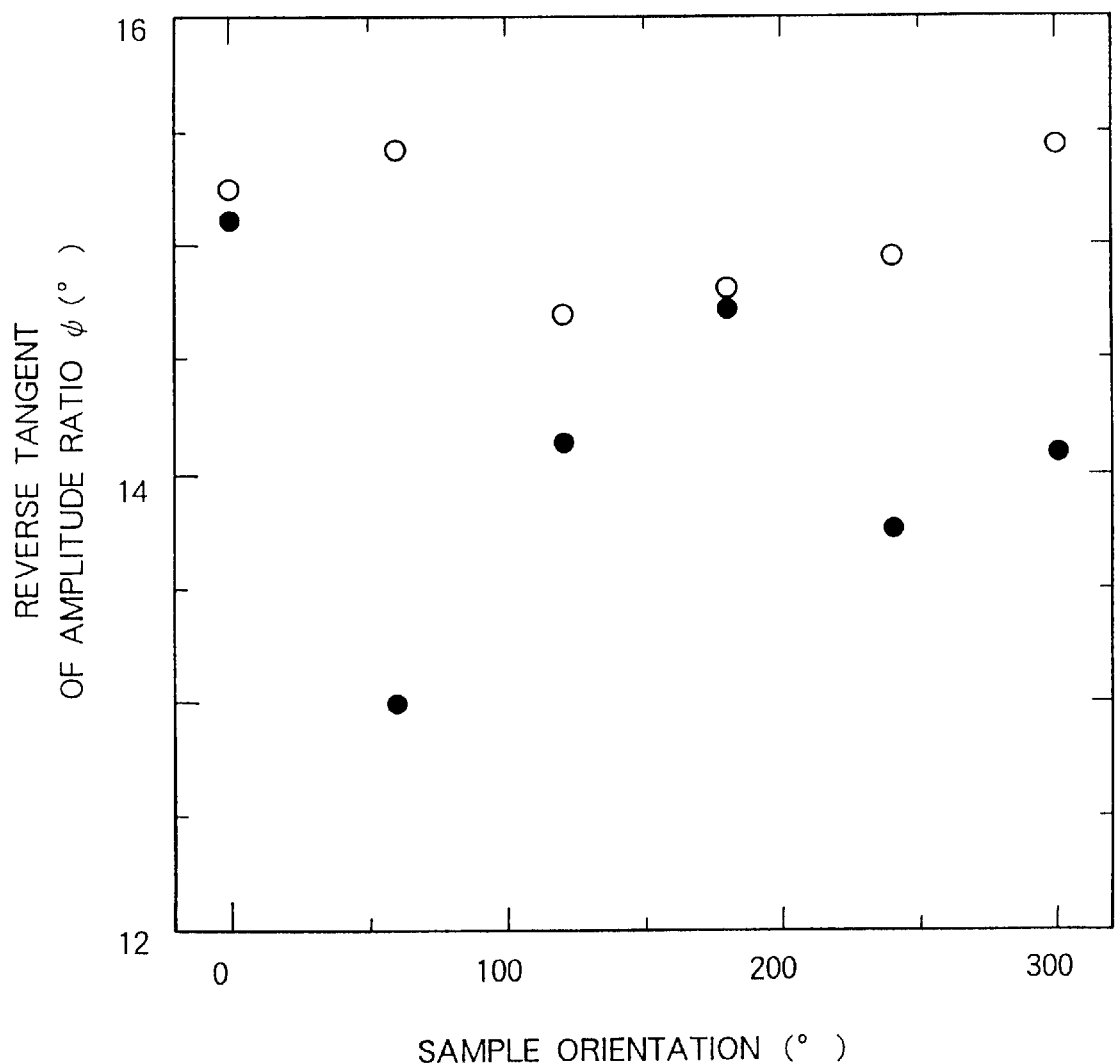
FIG. 8 is a graph showing an incidence orientation dependency of a reverse tangent ψ of an amplitude ratio for a peak at a wave number of 1500 cm$^{-1}$.

FIG. 7 is a graph showing the dependency of the phase difference Δ on incident orientation for a peak with a wave number of 1500 $cm^{-1}$. FIG. 8 is a graph showing the dependency of the reverse tangent ψ of an amplitude ratio on incident orientation for a peak with a wave number of 1500 $cm^{-1}$. In FIGS. 7 and 8, a symbol of white circle (○) indicates a result for the sample (reference sample) which was not subjected to rubbing processing and a black circle (●) indicates a result for the sample (sample C) subjected to rubbing processing.

As shown in FIGS. 7 and 8, with respect to both the phase difference Δ and the reverse tangent ψ of the amplitude ratio, the difference of the polarization state due to that of the incident orientation for the sample which was subjected to rubbing processing was larger than that for the sample which was not subjected to rubbing processing. By using the evaluation apparatus in this embodiment, therefore, it can be seen that rubbing processing caused anisotropy to occur to the molecular orientation.

If the measurement was conducted under a nitrogen gas atmosphere, time required to purge moisture and the like remaining in the container 1 was slightly reduced to about 40 minutes; however, no other big difference from the above-stated measurement was not seen.

Next, the second embodiment according to the present invention will be described. In this embodiment, the container 1 is made of stainless steel and the shape of each aperture is elliptical.

To shorten purging time for replacing atmosphere, it is effective to evacuate the container and to re-introduce a gas. The acrylic container 1 used in the first embodiment is not, however, resistant to the difference of pressure between inside and outside thereof. In the second embodiment, therefore, a stainless container 1 was used. The method of adjusting the infrared optical path and that of adjusting the position of a sample are the same as those in the preceding first embodiment.

Figure 9:
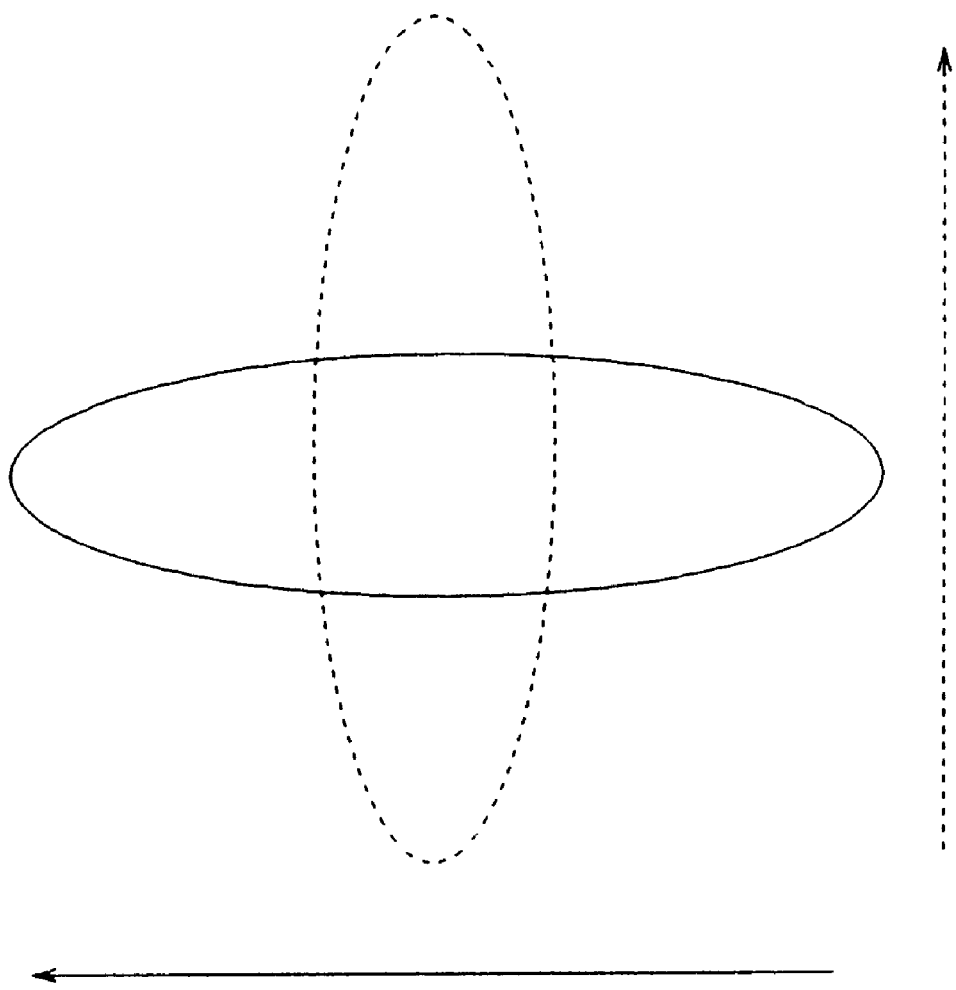
FIG. 9 is a typical view showing a change of a region onto which an infrared ray is applied, according to a change of incidence orientation.

If an infrared beam having a circular section narrowed by a circular aperture is used, the infrared beam is incident aslant on the sample surface. Owing to this, the shape of a region on the sample surface to which the infrared beam is applied becomes that of an ellipse having a longer axis in incident orientation. FIG. 9 is a typical view showing the change of the region applied with the infrared beam according to the change of the incident orientation. As shown in FIG. 9, as the incident orientation changes, the direction of the longer axis of this ellipse changes. As a result, measurement accuracy for measuring the dependency of the polarization state on incident orientation is lowered. Considering this, in the second embodiment, each of the apertures was set to have a shape of ellipse having a longer axis in S polarization direction. As a result, the region on the sample surface applied with the infrared beam became circular. Using such an aperture, the interior of the container 1 was evacuated with a rotary pump and then measurement was conducted to two samples (one which was subjected to rubbing processing and the other which was not subjected to rubbing processing). The sample formation method is the same as that in the first embodiment.

Figure 10:
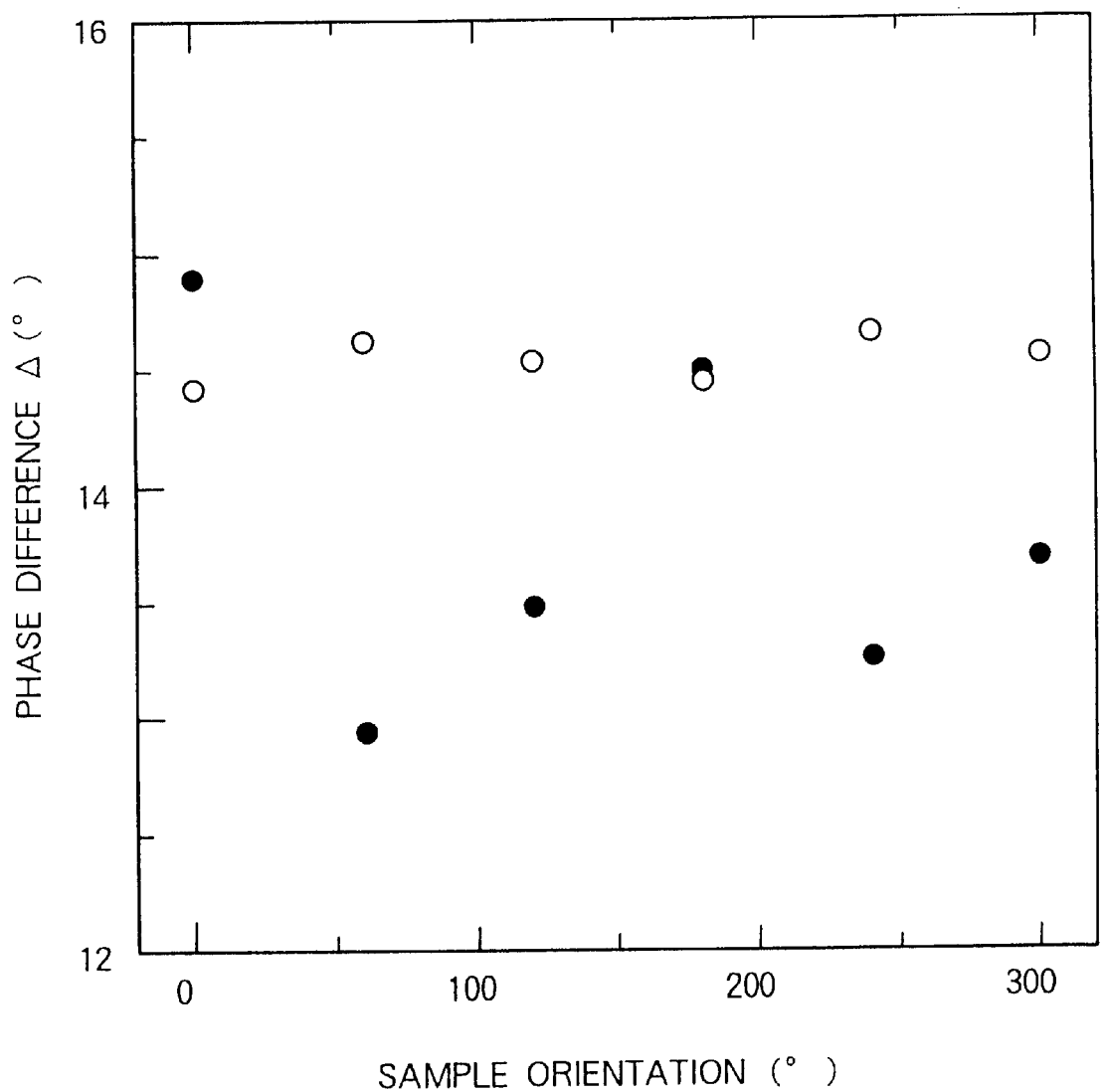
FIG. 10 is a graph showing an incidence orientation dependency of a phase difference Δ in the second embodiment according to the present invention.
Figure 11:
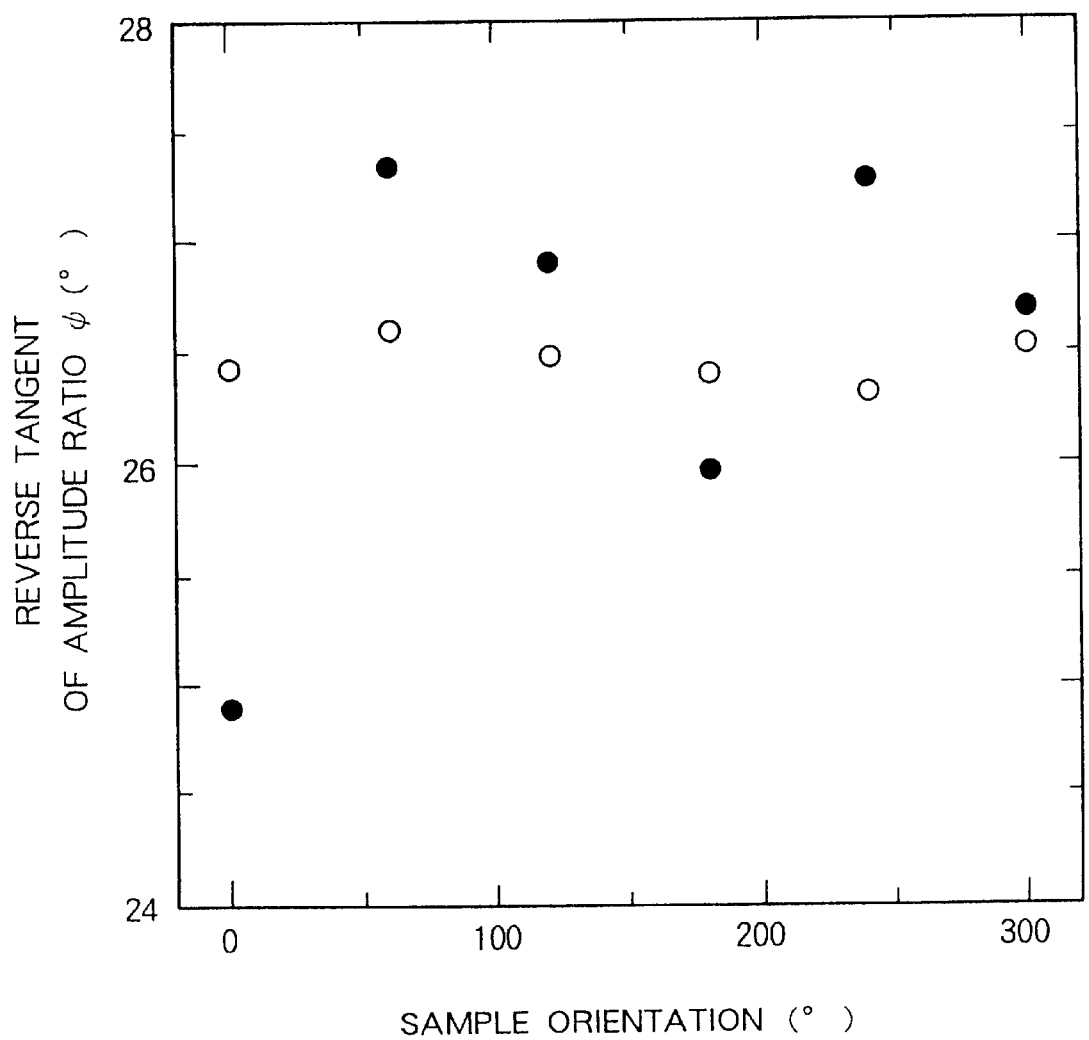
FIG. 11 is a graph showing an incidence orientation dependency of a reverse tangent ψ of an amplitude ratio in the second embodiment according to the present invention.

FIG. 10 is a graph showing the dependency of the phase difference Δ on the incident orientation in the second embodiment. FIG. 11 is a graph showing the dependency of the reverse tangent ψ of an amplitude ratio on incident orientation in the second embodiment. In FIGS. 10 and 11, a symbol of white circle (○) indicates a result for the sample which was not subjected to rubbing processing and that of black circle (●) indicates a result for the sample subjected to rubbing processing.

As shown in FIGS. 10 and 11, the sample which was not subjected to rubbing processing has low incident orientation dependency of both phase difference Δ and the reverse tangent ψ of the amplitude ratio, if comparing FIGS. 7 and 8 showing the measurement results in the first embodiment. From this, it is considered that the difference in the phase difference Δ and that in the reverse tangent of the amplitude ratio as seen in the first embodiment reflect the in-plane non-uniformity of the film.

If a cylindrical mirror instead of an elliptical aperture was put at the sample part in the FT-IR spectrometer 4 for introducing an infrared beam and the beam was reshaped, no preferential effect was not obtained by the first embodiment compared with the second embodiment, except that the intensity of the infrared beam became slightly higher.

Next, based on the data shown in FIGS. 10 and 11, a peak in the neighborhood of the a wave number of 1500 $cm^{-1}$ corresponding to phenyl-radicals contained in polyimide was noticed and the direction of phenyl-radicals was determined by the following method.

First, the dependency of the polarization state of a reflected infrared ray on incident orientation was measured. In this case, the polarization state of a reflected infrared ray was calculated by using a matrix of four rows by four columns. A matrix of four rows by four columns corresponding to the polyimide film is the same as described above. The elements $\Delta_{14}$, $\Delta_{24}$, $\Delta_{31}$, $\Delta_{32}$, $\Delta_{33}$, $\Delta_{41}$, $\Delta_{42}$ and $\Delta_{44}$ of the matrixes of four rows by four columns of the incident light and reflection light passing through an inert gas such as a nitrogen gas or a rare gas were 0. The remaining elements were as follows:

$\Delta_{11}=0$,
$\Delta_{12}=1-\sin^2 \beta$,
$\Delta_{13}=0$,
$\Delta_{21}=1$,
$\Delta_{22}=0$,
$\Delta_{23}=0$,
$\Delta_{24}=1$,
$\Delta_{43}=1-\sin^2 \beta$, It is noted that in these matrixes, an axis parallel to the normal of the sample surface is defined as Z axis, that parallel to the incident plane of the infrared ray and to the sample surface defined as X axis and that perpendicular to the X and Z axes defined as Y axis. In the following description, the matrix of four rows by four columns in a film is defined as a matrix A, the matrix of four rows by four columns in an inert gas (nitrogen or rare gas) is defined as a matrix B and a film thickness is defined as d. Further, if the states of electromagnetic fields of the incident light, reflection light and transmitted light are defined as column vectors $\Phi_I$, $\Phi_r$ and $\Phi_t$ each having four electromagnetic field components $E_x$, $H_y$, $E_y$ and $—H_x$, respectively, these vectors satisfy the following relationship:

$$(\Phi_I + \Phi_r)\exp(-i\omega Az)\exp(-i\omega Bd) = \Phi_t,$$

where z is a distance from the sample surface and may be an arbitrary value. While $\Phi_I$ and $\Phi_r$ depend on the value of z, the reflectance from the sample does not depend on the value of z since it is calculated from the ratio of $\Phi_I$ to $\Phi_r$. Then, when z=0, the following formula is obtained:

$$(\Phi_I + \Phi_r)\exp(-i\omega Bd) = \Phi_t.$$

In this analysis, for the calculation of $\exp(-i\omega Bd)$, Taylor's expansion was used to expand $i\omega Bd$ and sections up to the 24th one were considered. Cayley-Hamilton's theorem was used to conduct the calculation of the exponentiation of B at high speed. Also, $\Phi_I$ is incident light and may be arbitrary. Further, $\Phi_t$ can be directly calculated from $\Phi_I$ according to Snell's law. From these results, it is possible to determine $\Phi_r$ univocally.

Meanwhile, the electric field components $E_{rx}$ and $E_{ry}$ of $\Phi_r$, S component $E_{rs}$ parallel to the sample surface of the reflected infrared ray and P component $E_{rp}$ perpendicular to the S component and the traveling directions of the infrared ray satisfy the following relationship:

$E_{rs}=E_{ry}$, $E_{rp}=E_{rx} \cos \beta$.

That is, the polarization state of the reflection light ($\Delta_r$, $\psi_r$) is determined by the following formula:

$\exp(i\Delta_r) \tan \psi_r = E_{rx} \cos \beta / E_{ry}$.

The above calculation is conducted for each measurement orientation.

Figure 12:
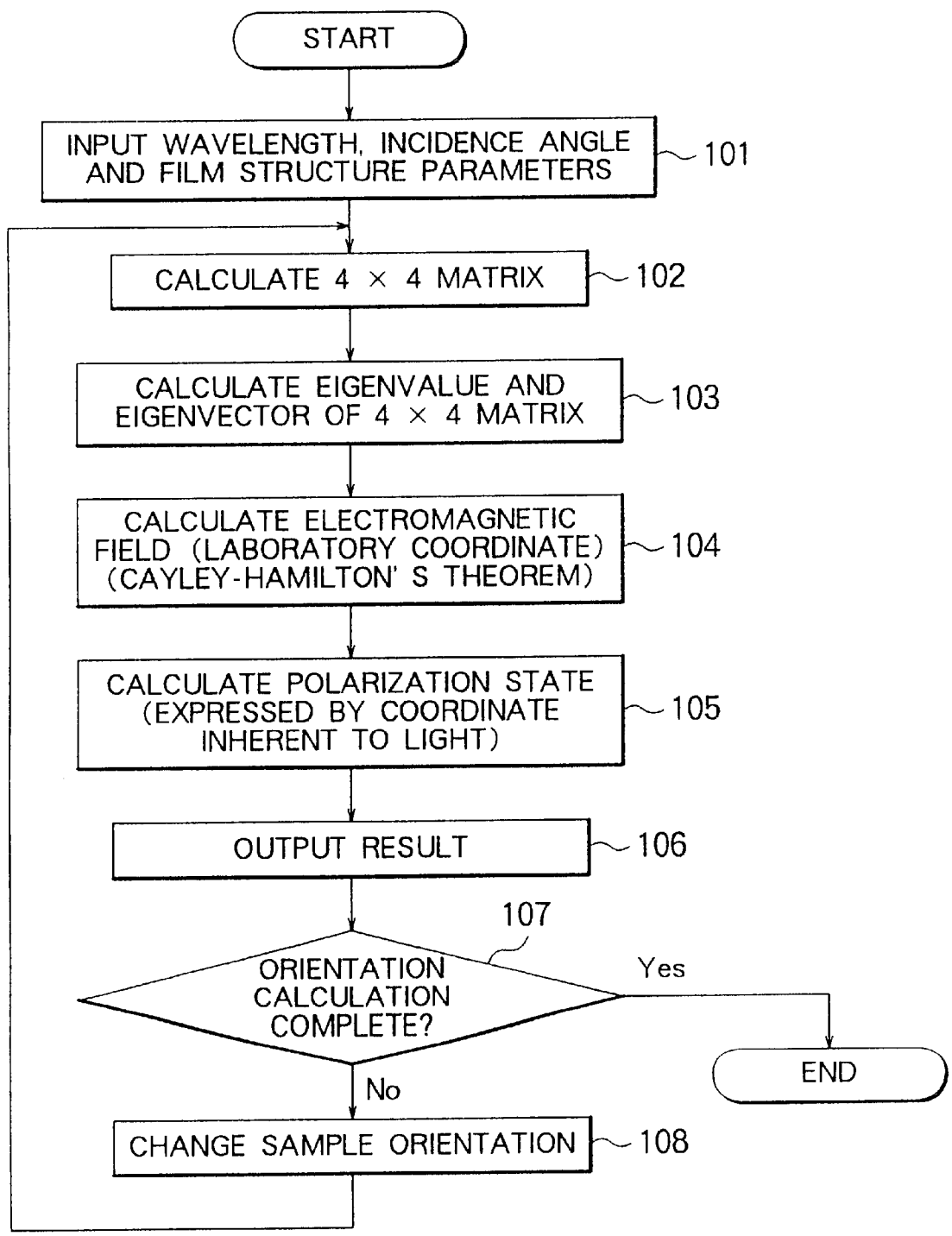
FIG. 12 is a flow chart showing a method of determining incidence orientation dependency.

FIG. 12 is a flow chart showing the method of determining incident orientation dependency.

First, a wavelength, an incidence angle and film structure parameters are inputted into a calculator (step S101). Matrixes of four rows by four columns are calculated (step S102). The eigenvalues and eigenvectors of the matrixes are calculated (step S103). Using the Cayley-Hamilton's theorem, the electromagnetic field in a laboratory coordinate system is calculated (step S104). A polarization state expressed by a coordinate inherent to light is calculated (step S105). The calculation result is outputted (step S106).

Next, it is judged whether or not calculations for all orientations are completed (step S107). If completed, processing procedures for the measurement of incident orientation dependency are finished. If not completed, sample orientation is changed (step S108) and processing procedures from the steps S102 to S107 are repeated.

Thereafter, the dependency of the polarization state of the reflected infrared ray on incident orientation calculated by the above procedures is compared with the measurement result and the film structure parameters are optimized so as to make the calculation result coincident with the measurement result. The parameters are optimized as follows.

If it is assumed that the target film is uniaxially anisotropic, the polarization state of the reflected light can be calculated using a matrix of four rows by four columns. The incident orientation dependency of a peak at a wave number of 1500 cm$^{-1}$ is noticed. Since the peak corresponds to the stretching vibration of phenyl-radicals, the molecular orientation of the phenyl-radical can be determined by determining the anisotropy of the absorption coefficient of the peak. While considering the presence of absorption, two anisotropic dielectric constants $\epsilon_e$, $\epsilon_o$ expressed by principal dielectric constant coordinate system become complex numbers and expressed by the following formulas, respectively:

$\epsilon_e = \epsilon_{er} + i\epsilon_{ei}$, $\epsilon_o = \epsilon_{or} + i\epsilon_{oi}$ where i is an imaginary unit.

In the film structure parameters, those four parameters ($\epsilon_{er}$, $\epsilon_{ei}$, $\epsilon_{or}$, $\epsilon_{oi}$) and the gradient angle $\theta$ of the principal dielectric constant coordinate system to the film surface and film thickness d are six parameters to be determined. In addition, two imaginary components ($\epsilon_{ei}$, $\epsilon_{oi}$) corresponding to absorption among the four components ($\epsilon_{er}$, $\epsilon_{ei}$, $\epsilon_{or}$, $\epsilon_{oi}$) of the dielectric constant which are quantities reflecting the regularity of the molecular orientation, give more direct information on the molecular orientation.

The values obtained by the above measurements are at six orientation if the entire circumference is measured at intervals of 60°. Thus, the obtained values are twelve values indicating the polarization state of the reflection light at six orientation. Therefore, the obtained values suffice to determine these six parameters indicating the film structure.

The respective measurement values, however, includes errors. Due to this, analytically obtained parameters may include large errors. Also, due to high non-linearity of the calculation formula, it is quite difficult to analytically determine six parameters.

Taking the above into consideration, it was decided that parameters were obtained by means of the method of least squares. Specifically, tentative values are substituted for six unknown parameters. The incident orientation dependency of the polarization state calculated from the above was compared with the measurement value and the values which sum of squares of the difference becomes a minimum was determined as a parameter. A total remainder R and a remainder $r_j$ at each measurement point (j-th measurement point) are defined as follows:

$R = \Sigma(W_1(\Delta_{obs}-\Delta_{cal})^2 + W_2(\psi_{obs}-\psi_{cal})^2)$, $r_j = W_1(\Delta_{obs}-\Delta_{cal})^2 + W_2(\psi_{obs}-\psi_{cal})^2$ where $\Delta_{obs}$ and $\Delta_{cal}$ are the observed value and calculation value of a phase difference $\Delta$ at each incident orientation, respectively, and $\psi_{obs}$, $\psi_{cal}$ are the observed value and calculation value of the reverse tangent $\psi$ of an amplitude ratio at each incident orientation, respectively. Also, $W_1$ and $W_2$ are weights (weighting coefficients). These weighting coefficients adjust the priority as to whether the coincidence of the phase difference $\Delta$ has preference to the coincidence of the reverse tangent $\psi$ of the amplitude ratio in optimizing. The sum ($\Sigma$) is obtained for all of measurement orientations. In this case, the number of measurement orientations is six, as described above.

The calculation by the method of least squares was mainly based on the corrected Marquardt method and a calculation algorithm was based on Koyanagi, "Data analysis by the method of least squares" (The University of Tokyo Press). Specifically, to determine the parameter dependency of the total remainder R, the six parameters each determining a remainder $r_j$ at each measurement orientation are partially differentiated and a differential matrix including the calculation results as matrix elements was determined. As a result, a matrix A of six rows by six columns was obtained. Further, a column matrix B including remainder $r_j$ as elements is defined. Then, a column vector P parameter satisfying the following formula is a correction vector:

$AP=B$

This value is added to parameters used for calculating the matrixes A and B, as a new film structure parameter. Until the measurement result coincides with the calculation result, these steps are continued as basic steps.

Since non-linearity is high in the calculation of film structure parameters, the total remainder after correction obtained by the parameters corrected according to the method is not exactly lower than that before correction. Due to this, operation for halving the correction vector value is repeated until the total remainder R becomes lower than that before correction. If the total remainder does not decrease even by repeating the step of halving the magnitude of the correction vector is repeated four times, an arbitrary number is added to diagonal elements of the differential matrix (damping) and the correction vector is calculated. The added value is based on one-fourth of the value of the determinant of the matrix A. As for the correction vector obtained by the respective damping operations, the value of the correction vector is halved four times or less until the total remainder becomes lower than that before correction. If the total remainder does not decrease even by the damping addition, the operation of increasing the damping value by four-fold is conducted up to five times.

Figure 13:
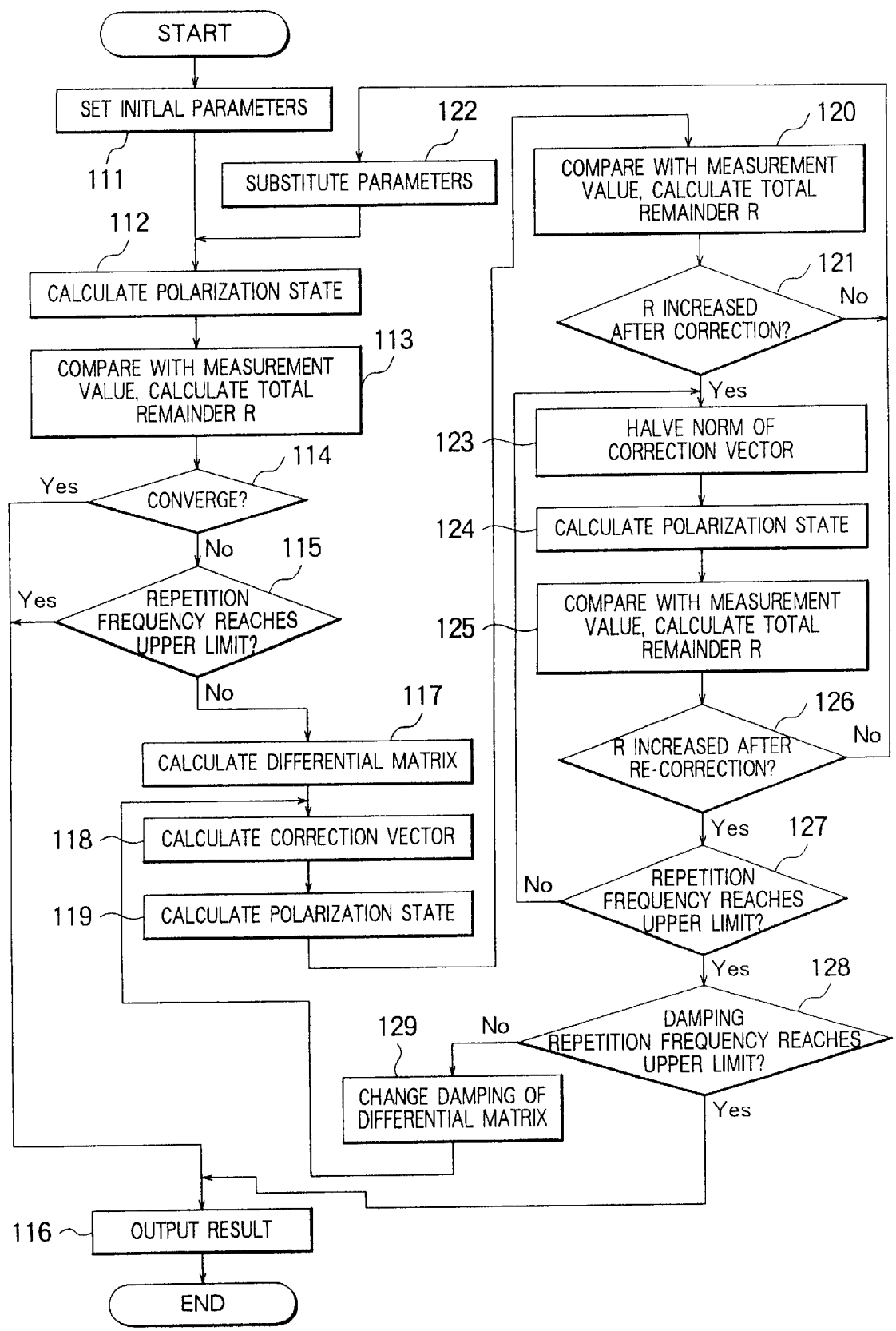
FIG. 13 is a flow chart showing a method of optimizing film structure parameters.

FIG. 13 is a flow chart showing the method of optimizing film structure parameters.

First, initial parameters are set (step S111). A polarization state is calculated (step S112). The calculation value and the measurement value are compared with each other and a total remainder R is calculated (step S113). Then, it is judged whether the total remainder R satisfies a predetermined convergence condition (step S114). If it satisfies the convergence condition, the result is outputted (step S116) and processing procedures are finished.

On the other hand, in a step S114, if the total remainder R does not satisfy the convergence condition, it is judged whether the repetition frequency has reached the upper limit (step S115). If the repetition frequency reached the upper limit, the result is outputted (step S116) and processing procedures are finished.

If the repetition frequency does not reach the upper limit in the step S115, the differential matrix A is calculated (step S117). The correction vector P is calculated (step S118). Next, the polarization state is calculated based on new film structure parameters obtained by adding the correction vector P to the film structure parameters (step S119). The calculation value and the measurement value are compared with each other and the total remainder R is calculated (step S120). It is judged whether the total remainder R after correction increased from that before correction (step S121). If the total remainder R did not increase, parameters obtained in the step S119 are substituted for the film structure parameters (step S122). Then, steps starting from the step S112 are repeated.

If the total remainder R increased in the step S121, the norm of the correction vector is halved (step S123). Next, the polarization state is calculated (step S124). The calculation value is compared with the measurement value and the total remainder R is calculated (step S125). It is then determined whether or not the total remainder R after correction increased from that before correction (step S126).

If the total remainder R did not increase in the step S126, the film structure parameters obtained in the step S119 are substituted for the parameters (step S122) and steps starting from the step S112 are repeated.

If the total remainder R increased in the step S126, it is then judged that the repetition frequency for halving the norm of the correction vector reaches the upper limit (step S127). If the repetition frequency does not reach the upper limit, the procedure returns to the step S123 and the steps of halving the norm of the correction vector are repeated.

If the repetition frequency reaches the upper limit in the step S127, it is then judged whether the repetition frequency for adding the damping to the differential matrix A reaches the upper limit (step S128). If the damping frequency reaches the upper limit in the step S128, the result is outputted (step S116) and the procedures are finished.

If the damping frequency does not reach the upper limit in the step S128, the damping of the differential matrix A is changed (step S129). Thereafter, the steps starting from the step S118 are repeated.

In this way, the film structure parameters can be optimized by the method of least squares.

When the film structure parameters were optimized based on the above-stated measurement results for the sample in this embodiment, the following result was obtained: the film thickness d was about 54 nm; the gradient angle of the principal dielectric constant coordinate was about 63°; and $\epsilon_{oi}$ and $\epsilon_{ei}$ were 1.0 and 1.2, respectively.

By considering that the absorption coefficient in the in-plane direction of the six-membered ring of phenyl-radicals and that in the normal direction of the plane thereof are 1:2, it could be determined that about 60% of the overall phenyl-radicals were oriented in a state in which the plane of six-membered ring was inclined at 27° (=90°−63°) from the sample surface. It is noted that the value of 'about 60%' is obtained from $(1.2/1.0)\times(\frac{1}{2})=0.6$.

Figure 14:
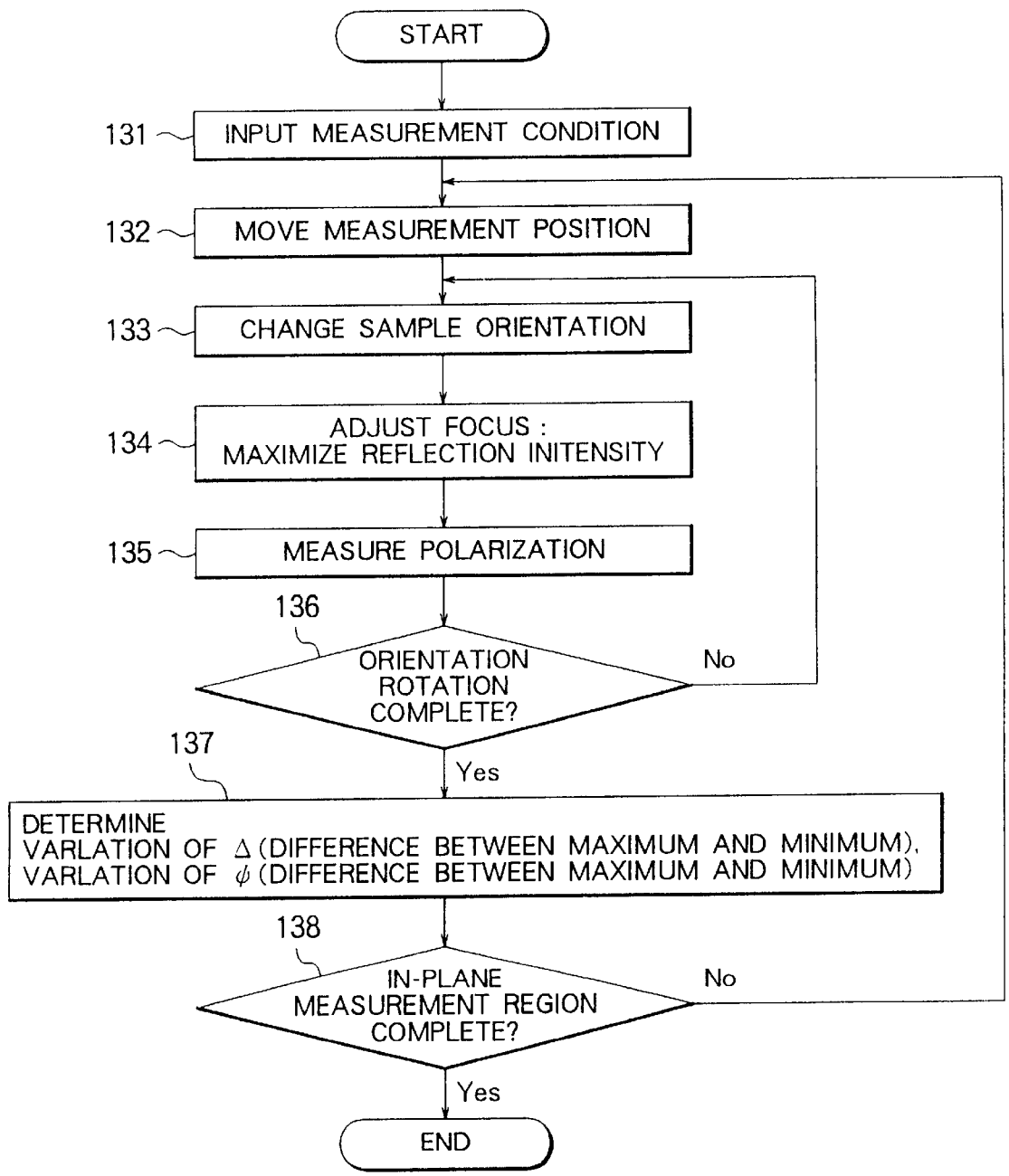
FIG. 14 is a flow chart showing a method of a control using a computer 14.

Next, the third embodiment according to the present invention will be described. In the third embodiment, the apparatus and samples having the same constitution as those of the apparatus and samples in the second embodiment were used and in-plane distribution was measured by the movement of the stage 10. This measurement was automatically made under the control of the computer 14. FIG. 14 is a flow chart showing the control method using the computer 14.

First, measurement conditions are inputted into the computer 14 (step S131). The sample is moved to a measurement position by the control of the computer 14 (step S132). The orientation of the sample is changed (step S133). Thereafter, focus adjustment is made to maximize the reflection intensity (step S134). Polarization is then measured (step S135).

Next, it is judged whether measurements for predetermined orientations have been finished, i.e., whether orientation rotation is completed (step S136). If orientation rotation is not completed, the procedures return to the step S133, in which the sample orientation is changed and measurement procedures are repeated.

On the other hand, if it is judged that orientation rotation is completed in the step S136, the variation (difference between a maximum and a minimum) of the phase difference $\Delta$ at the measurement position and the variation (difference between a maximum and a minimum) of the reverse tangent $\psi$ of the amplitude ratio are determined (step S137).

Thereafter, it is judged whether measurements at all measurement positions of the sample are completed, i.e., whether measurement in the in-plane measurement region is completed (step S138). If the measurement in the in-plane measurement region is completed, processing is finished. If not completed, the procedure returns to the step S132, in which the measurement position is moved, the sample is moved to the next measurement point and the above processing procedures are repeated.

In the third embodiment, the height of the sample was optimized from the reflection intensity at the first measurement point and the optical tilt angle was adjusted using the autocollimator 11 as in the case of the first embodiment. Then, as in the case of the first embodiment, the incident orientation dependency of the polarization state of the reflected infrared ray was measured by rotating the sample. Thereafter, the parallel translation stages 22 and 23 were controlled to move the sample to a predetermined position. By rotating the sample, the incident orientation dependency of the reflected infrared ray at that point was measured. Here, six points put horizontally and vertically, respectively at intervals of 5 mm in a grid-like manner, i.e., a total of 36 points were measured in a square region having a side of 25 mm. It is noted that the incident orientation interval at that moment was 60° for every point.

Figure 15:
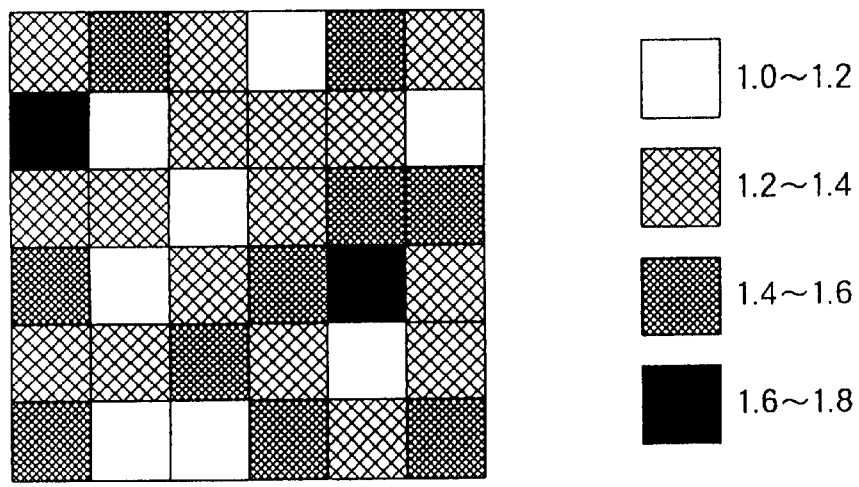
FIG. 15 is a typical view showing a distribution of a difference between the maximum and minimum of a phase difference Δ components for a peak at a wave number of 1500 cm$^{-1}$ obtained by the third embodiment according to the present invention.

FIG. 15 is a typical view showing the distribution of the differences between the maximum and minimum of the phase difference Δ component of a peak at a wave number of 1500 cm⁻¹ in the third embodiment. The difference between the maximum and minimum of the phase difference Δ component reflects the regularity of the molecular orientation as well as film thickness. The in-plane distribution of the irregularities of the film thickness was about 10%. Therefore, it may be considered that the observed distribution of the difference between the maximum and minimum of the phase difference Δ components reflects the regularity of the orientation of phenyl-radicals.

Figure 16:
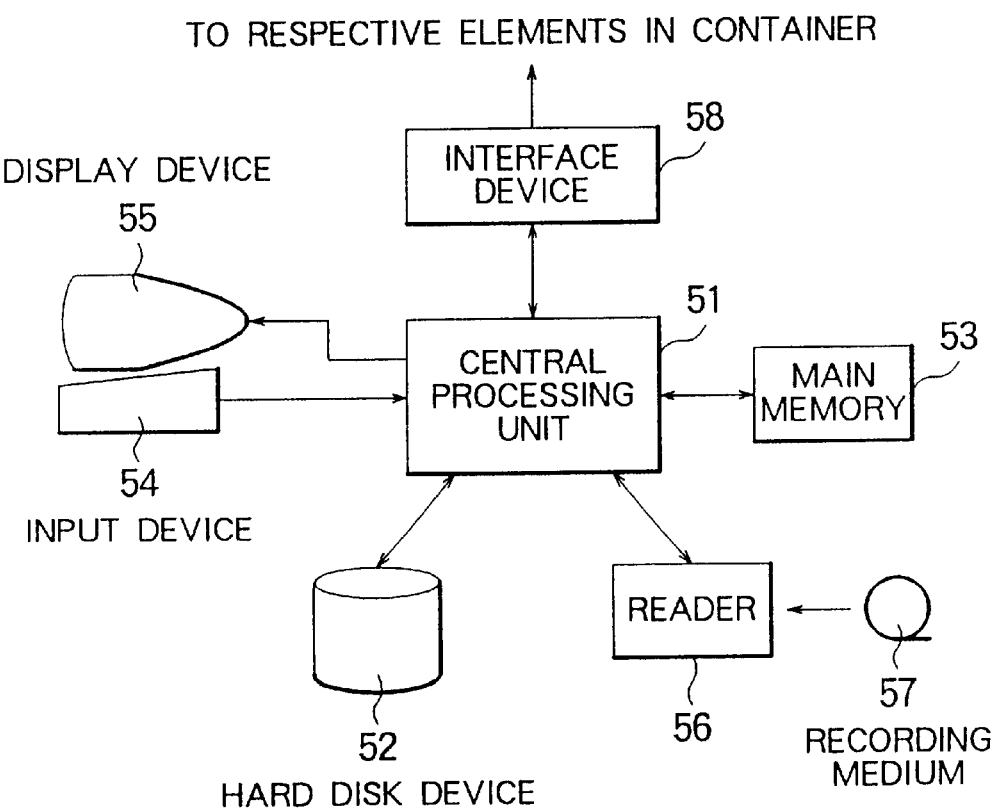
FIG. 16 is a block diagram showing a concrete structure of a computer system used as the computer 14 for the evaluation apparatus shown in FIG. 1.

The preferred embodiments of the present invention have been described so far. As described in the third embodiment, it is preferable that measurement is automatically conducted using a computer. FIG. 16 is a block diagram showing a concrete constitution of a computer system used as the computer 14 in an evaluation apparatus shown in FIG. 1.

The computer system is provided with, for example, a central processing unit (CPU) 51, a hard disk device 52 storing programs and data, a main memory 53 and input device 54 such as a keyboard and a mouse. The computer system is also provided with a display device 55 such as a CRT, a reader 56 reading data recorded on a recording medium 57 such as a magnetic tape and a CD-ROM and an interface device 58.

The interface device 58 connects the FT-IR spectrometer 4, the photoelastic element 6, the detector 8 and the stage 10 within the container 1 shown in FIG. 1 to the CPU 51. These constituent elements are controlled through the interface device 58 by the CPU 51 and signals outputted therefrom are received by the CPU 51.

Further, the hard disk device 52, the main memory 53, the input device 54, the display device 55, the reader 56 and the interface device 58 are connected to the CPU 51.

In the computer system constituted as described above, the recording medium 57 storing a program for, for example, allowing the measurements executed in the respective embodiments to be automatically conducted, can be installed at the reader 56. Then, the program is read from the recording medium 57 and stored in the hard disk device 52. The program stored in the hard disk device 52 is executed by the CPU 51, thereby making it possible to automatically conduct above-described measurements.

As described so far, according to the present invention, it is possible to determine the molecular orientation state and thickness of an organic thin film such as a liquid crystal alignment film formed on a glass substrate, by measuring the dependency of the polarization state of a reflected infrared ray on incident orientation. In addition, the in-plane distribution of the molecular orientation state can be automatically measured by using a sample stage provided with parallel stages moving in different two direction on the rotary stage controlled by the computer. Moreover, the irregularities of the measurement values due to the in-plane non-uniformity of the sample film can be reduced by using an elliptical aperture or a cylindrical mirror to make the shape of the infrared ray applied onto the sample surface circular.

What is claimed is:

1. A method of evaluating molecular orientation in a thin film, comprising the steps of:

analyzing dependency of a polarization state of a reflected infrared ray which is generated when an infrared ray in a fixed polarization state is incident on a sample thin film on incidence orientation, while rotating said sample thin film in a plane parallel to a surface thereof;

determining optical anisotropy of said sample thin film based on said dependency of polarization state on incidence orientation; and determining a state of molecular orientation in said sample thin film based on said optical anisotropy.

2. A method of evaluating molecular orientation in a thin film, comprising the steps of:

analyzing dependency of a polarization state of a reflected infrared ray which is generated when an infrared ray in a fixed polarization state is incident on a sample thin film on incidence orientation at a plurality of measurement points on said sample thin film, while rotating said sample thin film in a plane parallel to a surface thereof; and obtaining an in-plane distribution of a state of molecular orientation in said sample thin film based on measurement results at said respective measurement points.

3. The method according to claim 1, wherein said polarization state is indicated by a phase difference between two polarization components of said reflected infrared ray orthogonal to each other and a reverse tangent of an amplitude ratio of said two polarization components.

4. The method according to claim 2, wherein said polarization state is indicated by a phase difference between two polarization components of said reflected infrared ray orthogonal to each other and a reverse tangent of an amplitude ratio of said two polarization components.

5. The method according to claim 1, wherein the step of measuring said dependency of said polarization state of said reflected infrared ray on incident orientation is conducted while said sample thin film and optical paths of said incident infrared ray and said reflected infrared ray are arranged in an inert gas.

6. The method according to claim 2, wherein the step of measuring said dependency of said polarization state of said reflected infrared ray on incident orientation is conducted while said sample thin film and optical paths of said incident infrared ray and said reflected infrared ray are arranged in an inert gas.

7. The method according to claim 1, wherein the step of analyzing said dependency of said polarization state of said reflected infrared ray on incident orientation is conducted while said sample thin film and optical paths of said incident infrared ray and said reflected infrared ray are arranged in a vacuum.

8. The method according to claim 2, wherein the step of analyzing said dependency of said polarization state of said reflected infrared ray on incident orientation is conducted while said sample thin film and optical paths of said incident infrared ray and said reflected infrared ray are arranged in a vacuum.

9. The method according to claim 1, wherein a region applied with said incident infrared ray on said sample thin film is substantially circular.

10. The method according to claim 2, wherein a region applied with said incident infrared ray on said sample thin film is substantially circular.

11. An apparatus for evaluating molecular orientation in a thin film, comprising:

a light source which generates an infrared ray in a fixed polarization state and causes said infrared ray to be incident on a sample thin film;

a rotary stage which rotates said sample thin film in a plane parallel to a surface thereof;

a detector which detects an infrared ray reflected from said sample thin film; and an analyzer which analyzes dependency of a polarization state of said reflected infrared ray detected by said detector on incidence orientation, while said rotary stage rotating said sample thin film in the plane parallel to the surface thereof, determines optical anisotropy of said sample thin film from said dependency of said polarization state on incidence orientation, and determines a state of molecular orientation in said sample thin film based on said optical anisotropy.

12. The apparatus for evaluating molecular orientation in a thin film according to claim 11, which further comprising a controller which controls said rotary stage and said light source and receives detection data from said detector to rotate said sample thin film in the plane parallel to the surface thereof and automatically measure said dependency of said polarization state of said reflected infrared ray on incidence orientation.

13. An apparatus for evaluating molecular orientation in a thin film, comprising:

a light source which generates an infrared ray in a fixed polarization state and causes said infrared ray to be incident on a sample thin film;

a rotary stage which rotates said sample thin film in a plane parallel to a surface thereof;

a parallel translation stage which moves said sample thin film in a line in the plane parallel to the surface thereof;

a detector which detects an infrared ray reflected from said sample thin film; and an analyzer which analyzes dependency of a polarization state of said reflected infrared ray detected by said detector on incidence orientation at a plurality of measurement points of said sample thin film, while said rotary stage rotating said sample thin film in the plane parallel to the surface thereof and said parallel translation stage scanning said sample thin film, and determines a state of molecular orientation in said sample thin film based on measurement results at said respective measurement points.

14. The apparatus for evaluating molecular orientation in a thin film according to claim 13, which further comprising a controller which controls said rotary stage, said parallel translation stage and said light source and receives detection data from said detector to rotate said sample thin film in the plane parallel to the surface thereof and automatically measure said dependency of said polarization state of said reflected infrared ray on incidence orientation.

15. The apparatus for evaluating molecular orientation in a thin film according to claim 11, wherein said polarization state is indicated by a phase difference between two polarization components of said reflected infrared ray orthogonal to each other and a reverse tangent of an amplitude ratio of said two polarization components.

16. The apparatus for evaluating molecular orientation in a thin film according to claim 13, wherein said polarization state is indicated by a phase difference between two polarization components of said reflected infrared ray orthogonal to each other and a reverse tangent of an amplitude ratio of said two polarization components.

17. The apparatus for evaluating molecular orientation in a thin film according to claim 11, wherein said sample thin film and optical paths of said incident infrared ray and said reflected infrared ray are arranged in an inert gas.

18. The apparatus for evaluating molecular orientation in a thin film according to claim 13, wherein said sample thin film and optical paths of said incident infrared ray and said reflected infrared ray are arranged in an inert gas.

19. The apparatus for evaluating molecular orientation in a thin film according to claim 11, wherein said sample thin film and optical paths of said incident infrared ray and said reflected infrared ray are arranged in a vacuum.

20. The apparatus for evaluating molecular orientation in a thin film according to claim 13, wherein said sample thin film and optical paths of said incident infrared ray and said reflected infrared ray are arranged in a vacuum.

21. The apparatus for evaluating molecular orientation in a thin film according to claim 11, wherein said light source includes a Fourier transform infrared spectrometer and a polarizer.

22. The apparatus for evaluating molecular orientation in a thin film according to claim 13, wherein said light source includes a Fourier transform infrared spectrometer and a polarizer.

23. The apparatus for evaluating molecular orientation in a thin film according to claim 11, wherein a region applied with said incident infrared ray on said sample thin film is substantially circular.

24. The apparatus for evaluating molecular orientation in a thin film according to claim 13, wherein a region applied with said incident infrared ray on said sample thin film is substantially circular.

25. A computer-readable recording medium, storing a program for causing a computer to conduct the processes for:

controlling a rotary stage to rotate a sample thin film in a plane parallel to a surface thereof;

receiving detection data from a detector and analyzing dependency of a polarization state of a reflected infrared ray which is generated when an infrared ray in a fixed polarization state from a light source is incident on said sample thin film on incidence orientation; and determining a state of molecular orientation in said sample thin film based on said dependency of said polarization state on incidence orientation.

26. A computer-readable recording medium, storing a program for causing a computer to conduct the processes for:

controlling a rotary stage to rotate a sample thin film in a plane parallel to a surface thereof;

controlling a parallel translation stage to move said sample thin film in a line in the plane parallel to the surface thereof;

receiving detection data from a detector and analyzing dependency of a polarization state of a reflected infrared ray which is generated when an infrared ray in a fixed polarization state from a light source is incident on said sample thin film on incidence orientation at a plurality of measurement points on said sample thin film; and determining a state of molecular orientation in said sample thin film based on said dependency of said polarization state on incidence orientation at said respective measurement points.

* * * * *